(12) United States Patent
Schwab et al.

(10) Patent No.: US 10,912,878 B2
(45) Date of Patent: Feb. 9, 2021

(54) SEAT AND COVER SYSTEM WITH MEDICAL UNITS

(71) Applicant: Whole Bath, LLC., East Chatham, NY (US)

(72) Inventors: Brian Schwab, East Chatham, NY (US); Shao-Yu Peng, Changhau County (TW)

(73) Assignee: Whole Bath, LLC, East Chatham, NY (US)

( * ) Notice: Subject to any disclaimer, the term of this patent is extended or adjusted under 35 U.S.C. 154(b) by 0 days.

(21) Appl. No.: 15/588,638

(22) Filed: May 6, 2017

(65) Prior Publication Data

US 2017/0319794 A1    Nov. 9, 2017

Related U.S. Application Data

(60) Provisional application No. 62/333,152, filed on May 6, 2016.

(51) Int. Cl.
*A61M 3/02* (2006.01)
*B05B 15/656* (2018.01)
(Continued)

(52) U.S. Cl.
CPC ........... *A61M 3/0279* (2013.01); *A47K 10/48* (2013.01); *A47K 13/24* (2013.01); *A61M 3/0225* (2013.01);
(Continued)

(58) Field of Classification Search
CPC ...................................................... E03D 9/08
See application file for complete search history.

(56) References Cited

U.S. PATENT DOCUMENTS

| 2,875,450 A | 3/1959 | Umann |
| D198,085 S | 4/1964 | Rich |

(Continued)

FOREIGN PATENT DOCUMENTS

| EM | 025022450001 | 7/2014 |
| EP | 2138640 | 12/2009 |

(Continued)

OTHER PUBLICATIONS

PCT Notification of Transmittal of the International Search Report and the Written Opinion of the International Searching Authority, or Declaration; PCT/US2017/031485, filed on May 6, 2017 by Whole Bath, LLC.

(Continued)

*Primary Examiner* — Janie M Loeppke
(74) *Attorney, Agent, or Firm* — Michael D. Eisenberg

(57) ABSTRACT

Aspects of the present invention provide a method for using an apparatus to deliver medicine and to wash, clean, and dry a region of a human body. The apparatus include a toilet seat assembly and a medicine delivery assembly. In addition, the apparatus may include a drying nozzle assembly and/or a spraying nozzle assembly. The medicine delivery assembly may include one or more medicine storage cartridges and/or one or more medicine base units, each medicine base unit includes at least a cartridge unit and at least a cartridges slot, wherein the cartridge slot is adapted to match with a medicine storage cartridge. The medicine delivery assembly may include a medicine delivery nozzle, which can be coupled to a spraying nozzle assembly, or may be operated by itself with a medicine delivery nozzle. Finally, the medicine delivery assembly can be controlled by one or more control units.

24 Claims, 16 Drawing Sheets

(51) Int. Cl.
  *B05B 15/70* (2018.01)
  *A47K 10/48* (2006.01)
  *A47K 13/24* (2006.01)
  *E03D 9/08* (2006.01)
  *B05B 1/00* (2006.01)
  *B05B 13/04* (2006.01)

(52) U.S. Cl.
  CPC ........ *A61M 3/0245* (2013.01); *A61M 3/0258* (2013.01); *B05B 1/005* (2013.01); *B05B 15/656* (2018.02); *B05B 15/70* (2018.02); *E03D 9/08* (2013.01); *A61M 2210/1067* (2013.01); *B05B 13/0405* (2013.01)

(56) References Cited

U.S. PATENT DOCUMENTS

| | | |
|---|---|---|
| 3,810,260 A | 5/1974 | Lodi |
| 3,995,326 A | 12/1976 | Umann |
| 4,279,362 A | 7/1981 | Pursell |
| 4,287,618 A | 9/1981 | Silver |
| 4,327,560 A | 5/1982 | Leon et al. |
| D266,758 S | 11/1982 | Johannsen |
| 4,422,189 A | 12/1983 | Couvrette |
| D279,184 S | 6/1985 | Sakamoto |
| 4,628,548 A | 12/1986 | Kurosawa et al. |
| D303,966 S | 10/1989 | Fritzsche |
| 4,903,347 A | 2/1990 | Garcia et al. |
| 4,987,617 A | 1/1991 | Furukawa et al. |
| 5,031,252 A | 7/1991 | Oyama |
| 5,101,520 A | 4/1992 | Lockhart |
| 5,201,080 A * | 4/1993 | Tanaka ............... E03D 9/08 4/443 |
| 5,203,037 A | 4/1993 | Kang |
| 5,247,711 A | 9/1993 | Kwon |
| 5,335,855 A | 8/1994 | Borod |
| D355,246 S | 2/1995 | Kawamura |
| 5,409,167 A | 4/1995 | Borod |
| D367,922 S | 3/1996 | Kobayashi |
| 5,504,948 A | 4/1996 | Chandler |
| 5,551,098 A | 9/1996 | Wilk |
| 5,566,402 A | 10/1996 | Agha el.Rifai et al. |
| 5,630,234 A | 5/1997 | Childs |
| D387,851 S | 12/1997 | Pieters |
| 5,720,054 A | 2/1998 | Nakayama et al. |
| 5,765,238 A | 6/1998 | Furukawa et al. |
| 5,813,060 A | 9/1998 | Klopocinski |
| 5,864,894 A * | 2/1999 | Fedele ............... E03D 9/08 4/213 |
| 5,898,956 A | 5/1999 | Kurisaki et al. |
| 5,911,516 A | 6/1999 | Chang |
| 5,953,765 A | 9/1999 | Hayashi et al. |
| 5,987,659 A | 11/1999 | Cannizzaro |
| 6,003,159 A | 12/1999 | Sadegh et al. |
| 6,009,570 A | 1/2000 | Hargest |
| D423,655 S | 4/2000 | Otte |
| 6,073,275 A | 6/2000 | Klopocinski |
| 6,105,178 A | 8/2000 | Kurisaki et al. |
| D432,220 S | 10/2000 | Hulsebus |
| 6,128,788 A | 10/2000 | Yamazaki |
| D435,638 S | 12/2000 | Merry |
| 6,167,577 B1 | 1/2001 | Hammad |
| 6,178,568 B1 | 1/2001 | Boulieris |
| 6,192,527 B1 | 2/2001 | Paul |
| D451,076 S | 11/2001 | Sommer et al. |
| D451,177 S | 11/2001 | Scholpp |
| 6,339,852 B1 | 1/2002 | Huang |
| 6,397,406 B1 | 6/2002 | Moshkovich |
| 6,449,780 B1 | 9/2002 | Merry |
| 6,481,590 B1 | 11/2002 | Simkins |
| D471,966 S | 3/2003 | Takahashi |
| D481,016 S | 10/2003 | Hillis |
| D485,337 S | 1/2004 | Tani |
| 6,688,500 B1 | 2/2004 | Cheng |
| 6,754,912 B1 | 6/2004 | Hayashi et al. |
| D500,130 S | 12/2004 | Jung |
| D508,733 S | 8/2005 | Peng |
| D512,425 S | 12/2005 | Nakagawa |
| 6,973,679 B1 | 12/2005 | Schad |
| 7,096,518 B2 | 8/2006 | Takenaga |
| D528,991 S | 9/2006 | Katsuyama et al. |
| 7,120,946 B1 | 10/2006 | Lazar |
| 7,127,750 B2 | 10/2006 | Lim |
| D533,788 S | 12/2006 | Kleiman |
| 7,155,755 B2 | 1/2007 | Olivier |
| D538,907 S | 3/2007 | Kaule |
| 7,191,473 B2 | 3/2007 | Matsomoto et al. |
| D541,225 S | 4/2007 | Katsuyama et al. |
| 7,216,374 B2 | 5/2007 | Hassan |
| 7,284,285 B2 | 10/2007 | Scalzi |
| 7,287,286 B2 | 10/2007 | Lee |
| D554,613 S | 11/2007 | Nakatani |
| D558,181 S | 12/2007 | Takada |
| D564,976 S | 3/2008 | Billings et al. |
| D565,554 S | 4/2008 | Fan |
| D578,515 S | 10/2008 | Ikeda et al. |
| D579,342 S | 10/2008 | Priestman |
| D583,030 S | 12/2008 | Kobayashi |
| D594,537 S | 6/2009 | Driedger |
| D594,945 S | 6/2009 | Nakasaki et al. |
| 7,543,339 B1 | 6/2009 | Harris |
| D608,426 S | 1/2010 | Watanabe |
| D616,445 S | 5/2010 | Wong et al. |
| D634,735 S | 3/2011 | Maier |
| D639,399 S | 6/2011 | Takeuchi |
| D639,400 S | 6/2011 | Kang |
| 7,954,181 B2 | 6/2011 | Lim |
| 8,060,953 B1 | 11/2011 | Dorra |
| D654,808 S | 2/2012 | Gidlow |
| 8,161,580 B2 | 4/2012 | Hashidume et al. |
| 8,261,377 B2 | 9/2012 | Oh |
| D668,642 S | 10/2012 | Feldman et al. |
| 8,291,527 B2 | 10/2012 | Pan et al. |
| D670,659 S | 11/2012 | Ishikawa et al. |
| D671,935 S | 12/2012 | Mao |
| 8,365,317 B1 | 2/2013 | Dorra |
| 8,425,475 B2 | 4/2013 | Sodo |
| D682,246 S | 5/2013 | Boqueho |
| D688,359 S | 8/2013 | Ogata et al. |
| D692,417 S | 10/2013 | Tu |
| D692,541 S | 10/2013 | Hosoi et al. |
| D698,754 S | 2/2014 | Vignau-Lous |
| D703,797 S | 4/2014 | Shinozaki |
| D704,316 S | 5/2014 | Yoshioka |
| D704,317 S | 5/2014 | Ando |
| D706,402 S | 6/2014 | Yeung |
| D708,954 S | 7/2014 | Barnes |
| 8,776,278 B1 | 7/2014 | Dorra |
| D713,815 S | 9/2014 | Ookawa |
| D715,774 S | 10/2014 | Lee et al. |
| D716,768 S | 11/2014 | Kim |
| D717,930 S | 11/2014 | Kergoet |
| 8,904,575 B1 | 12/2014 | Lindheimer et al. |
| D724,058 S | 3/2015 | Chandel |
| D724,059 S | 3/2015 | Kim |
| D750,765 S | 3/2016 | Giametta |
| 9,273,454 B2 | 3/2016 | Slawinski |
| 9,279,241 B2 | 3/2016 | Morioka et al. |
| D753,095 S | 4/2016 | Moran |
| 9,464,425 B2 | 10/2016 | Bailey |
| D781,808 S | 3/2017 | Pista |
| D792,867 S | 7/2017 | Murphy |
| D805,615 S | 12/2017 | Peng |
| 9,889,982 B2 | 2/2018 | Falcon |
| 2003/0140407 A1 | 7/2003 | Matsumoto et al. |
| 2004/0055080 A1 | 3/2004 | Marshall |
| 2005/0000006 A1* | 1/2005 | Takenaga ............ E03D 9/08 4/420.4 |
| 2005/0010997 A1 | 1/2005 | Olivier |
| 2006/0000012 A1 | 1/2006 | Schad |
| 2006/0265801 A1 | 11/2006 | Riccobon |
| 2007/0241929 A1 | 10/2007 | Marchetto |
| 2008/0047055 A1 | 2/2008 | Lim |
| 2008/0055394 A1 | 3/2008 | Shiue |

(56) References Cited

U.S. PATENT DOCUMENTS

| | | |
|---|---|---|
| 2008/0201837 A1 | 8/2008 | Oh |
| 2008/0251551 A1 | 10/2008 | Huber |
| 2009/0313752 A1 | 12/2009 | Kunimoto et al. |
| 2010/0012685 A1 | 1/2010 | Ramsey |
| 2010/0162475 A1* | 7/2010 | Hashidume ............... E03D 9/08 4/233 |
| 2010/0176224 A1 | 7/2010 | Hasselschwert |
| 2011/0132929 A1 | 6/2011 | Bennett |
| 2011/0191950 A1 | 8/2011 | Liu |
| 2011/0203044 A1 | 8/2011 | Lim |
| 2012/0005817 A1 | 1/2012 | Jeong |
| 2012/0011647 A1 | 1/2012 | Mochita |
| 2012/0150148 A1 | 6/2012 | Shi |
| 2012/0180785 A1 | 7/2012 | Trill |
| 2012/0266483 A1 | 10/2012 | Palermo et al. |
| 2013/0133131 A1 | 5/2013 | Peng |
| 2013/0180041 A1 | 7/2013 | Ding |
| 2013/0267890 A1 | 10/2013 | Li |
| 2014/0042195 A1 | 2/2014 | Geis |
| 2014/0047626 A1* | 2/2014 | Dorra ................... A47K 13/302 4/223 |
| 2014/0068862 A1 | 3/2014 | Al-Jafar |
| 2014/0101838 A1 | 4/2014 | Gupta et al. |
| 2014/0107409 A1 | 4/2014 | Bailey et al. |
| 2015/0000025 A1 | 1/2015 | Clements |
| 2015/0059076 A1 | 3/2015 | Tiagai |
| 2015/0203279 A1 | 7/2015 | Falcon |
| 2015/0225167 A1 | 8/2015 | Andersen |
| 2015/0337525 A1 | 11/2015 | Bailey |
| 2016/0316978 A1 | 11/2016 | Peng |
| 2017/0021116 A1 | 1/2017 | Rahmel |
| 2017/0142306 A1 | 5/2017 | Peng |
| 2017/0265624 A1 | 9/2017 | Wilson |
| 2017/0321406 A1 | 11/2017 | Schwab |
| 2017/0321407 A1 | 11/2017 | Schwab |
| 2017/0321408 A1 | 11/2017 | Schwab |
| 2018/0015238 A1 | 1/2018 | Schwab |
| 2018/0028797 A1 | 2/2018 | Schwab |
| 2018/0036473 A1 | 2/2018 | Schwab |
| 2018/0044903 A1 | 2/2018 | Schwab |

FOREIGN PATENT DOCUMENTS

| | | |
|---|---|---|
| EP | 2138640 A1 | 12/2009 |
| EP | 2742189 B1 | 10/2016 |
| IN | 2689190001 | 10/2015 |
| JP | H0893034 | 4/1996 |
| JP | H0988165 | 3/1997 |
| JP | H1163666 | 3/1999 |
| JP | 2001279778 | 10/2001 |
| WO | WO 2008/024005 A2 | 2/2008 |
| WO | 2013020240 | 2/2013 |
| WO | WO 2012/044086 A2 | 4/2017 |

OTHER PUBLICATIONS

PCT Notification of Transmittal of the International Search Report and the Written Opinion of the International Searching Authority, or Declaration, PCT/US2017/031482, filed on May 6, 2017 by Whole Bath, LLC.
PCT Notification of Transmittal of the International Search Report and the Written Opinion of the International Searching Authority, or Declaration, PCT/US2017/031483, filed on May 6, 2017 by Whole Bath, LLC.
PCT Notification of Transmittal of the International Search Report and the Written Opinion of the International Searching Authority, or Declaration; PCT/US2017/031484, filed on May 6, 2017 by Whole Bath, LLC.
Kohler, Self-Cleaning Wand, https://www.youtube.com/watch?y=z629hpdnWj8, published Oct. 12, 2016.
U.S. Appl. No. 15/847,594, filed Dec. 19, 2019, Brian Schwab.
Final Office Action for U.S. Appl. No. 15/588,640 dated Dec. 3, 2018.
PCT Notification of Transmittal of the International Search Report and the Written Opinion of the International Searching Authority, PCT/2017/031484, dated Aug. 14, 2017.
PCT Notification of Transmittal of the International Search Report and the Written Opinion of the International Searching Authority, PCT/US2016/45932, dated Oct. 24, 2016.
PCT Notification of Transmittal of the International Search Report and the Written Opinion of the International Searching Authority, PCT/US2017/042288, dated Sep. 28, 2017.
PCT Notification of Transmittal of the International Search Report and the Written Opinion of the International Searching Authority, PCT/US2017/42253, dated Nov. 21, 2017.
Schwabcare website 2017, http://schwabcare.com/, site visited Jan. 21, 2018.

* cited by examiner

SEAT AND COVER SYSTEM WITH MEDICAL UNITS

CROSS-REFERENCE TO RELATED APPLICATIONS

This application claims benefit of U.S. provisional patent application Ser. No. 62/333,152, filed May 6, 2016, which is herein incorporated by reference.

BACKGROUND OF THE INVENTION

Embodiments of the present invention generally relate to an apparatus and system for washing, cleaning, drying, and/or delivering medicine to a region of a human body. More specifically, aspects of the present invention provide a method and apparatus for delivering and applying water, medication, and/or a cleaning solution to a region of the body (e.g., genital or anal area, intimate parts, perianal region) which may be difficult for the user to access and dry the region.

DESCRIPTION OF THE RELATED ART

Bidets and other modern toilet seat systems have been used to spray water and clean private parts of a user using a toilet. The bidet systems are used for washing the genital and anal areas using cleaning water of appropriate temperature sprayed from the center of the bidet system, instead of a toilet paper after relief stool or urination. Originally being developed for washing the pubic area for females, bidet systems have now been popular among people of all ages and both sexes because it is known to be more hygienic to wash the intimate parts and anus with water instead of paper after relief. In addition, cleansing the pubic/anal regions with water may help to avoid infection and prevent hemorrhoids and other anal disease. Furthermore, it is very effective for women with gynecological diseases. It is also very useful for the elderly or obese people to relieve themselves with great convenience.

However, most bidets and bidet seat cleaning systems have water spray nozzle positioned near posterior or anal areas and thus is not suitable for washing and cleaning female anterior private parts. In addition, bidet systems are expensive and need to be pre-installed. Further, the drying mechanisms of most bidets and bidet seat systems are not movable freely or localized to the area that need to be dried. Also, most bidets and bidet seat systems are not equipped with appropriate cleaning solutions or medications that are stored and delivered in mechanisms that can be freely movable or being localized to the area that need to be cleaned. Therefore, there is a need for a convenient, easy to carry wash and clean apparatus for cleaning genital or anal area of a human body.

SUMMARY OF THE INVENTION

The present invention generally includes a method and an apparatus for delivering medicine, washing, cleaning, and drying a region of a human body. The apparatus includes a toilet seat assembly, and a medicine delivery assembly. In addition, the apparatus may include a drying nozzle assembly and/or a spraying nozzle assembly.

In one embodiment, the medicine delivery assembly of the invention includes one or more medicine storage cartridges and the medicine delivery assembly is adapted to deliver one or more medicine-containing solutions that are stored at the one or more medicine storage cartridges. In another embodiment, the medicine delivery assembly of the invention includes one or more medicine base units, each medicine base unit includes at least a cartridge unit and at least a cartridges slot, wherein the cartridge slot is adapted to match with a medicine storage cartridge.

In one aspect, the medicine storage cartridge includes a cartridge cover, a medicine inlet being connected to a medicine storage assembly, and a sensor for matching and identifying a medicine solution stored within the medicine storage assembly. In another aspect, the medicine storage assembly includes a medicine storage tank adapted for storing a medicine-containing solution, a tank cover, and a tubing which is connected to the medicine inlet of the medicine storage cartridge. In still another aspect, the medicine storage assembly further includes a medicine storage element adapted to store one or more medicines to be mixed with water to form into the medicine-containing solution.

In a yet another aspect, the medicine storage assembly further includes a liquid solution indicator adapted to indicate the content level of the medicine-containing solution within the medicine storage tank. Further, the medicine storage assembly may also include a pressurized pump adapted to pump and deliver the medicine-containing solution from the medicine storage tank into the toilet seat assembly.

In still another embodiment, the medicine delivery assembly of the invention includes one or more driving motors, one or more steering gears, and a medicine delivery nozzle having a nozzle body that is retractable, wherein the medicine delivery nozzle is adapted to deliver one or more medicine-containing solutions to the region of the human body. In one aspect, the medicine delivery nozzle includes an atomizer nozzle head adapted to atomize a medicine-containing solution to achieve a consistency that can be applied over a distance and deliver a stream of the medicine-containing solution to a user. In another aspect, the medicine delivery nozzle is adapted to deliver the medicine-containing solutions across a space to a perianal region of a user. In still another aspect, the medicine delivery assembly further includes a pressurized pump adapted to pump and deliver the medicine-containing solution from a medicine inlet of a medicine storage cartridge.

In still another embodiment, the apparatus of the invention further includes a spraying nozzle assembly, where the medicine delivery assembly includes a medicine delivery nozzle, which is separated from the spraying nozzle assembly. In yet another embodiment, the apparatus of the invention further includes a spraying nozzle assembly, where the medicine delivery assembly is coupled to a spray nozzle channel of the spraying nozzle assembly. In one aspect, the spray nozzle channel of the spraying nozzle assembly includes a nozzle jet head opening adapted to deliver a solution at high speed. In another aspect, the solution is selected form the group consisting of water, a cleaning solution, a barrier spray solution, a medicine-containing solution, and combinations thereof.

In yet another embodiment, the apparatus of the invention further includes a drying nozzle assembly, which comprises a fan, one or air channels connected to the fan, one or more drying nozzle units connected to the one or more air channels, and one or more driving motor units. In one aspect, the one or more driving motor units of the medicine delivery assembly includes one or more steering gears, a first driving motor being connected to the one or more drying nozzle units and the one or more steering gears, wherein the first driving motor is adapted to move the one or more drying nozzle units in retracting-and-extending motion. In another aspect, the one or more driving motor units of the medicine delivery assembly further includes a second driving motor being connected to the one or more drying nozzle units and the one or more steering gears, wherein the second driving motor is adapted to move the one or more drying nozzle units in three-dimensional circular rotational motion.

Another embodiment of the invention provides one or more control units connected to the toilet seat assembly and the medicine delivery assembly, where the control units are adapted to receive a user input and, based on the user input, to direct movements of one or more motors and adjust the positions of one or more nozzles within the toilet seat assembly and the medicine delivery assembly.

Still another embodiment of the invention provides a method for delivering one or more medicines to a region of a human body. The method includes providing one or more medicines to a medicine delivery assembly which is coupled to a toilet seat assembly, and controlling one or more movements of the medicine delivery assembly by one or more control units. In one aspect, wherein controlling the movements of the medicine delivery assembly includes directing one or more extending and retracting movements of a medicine delivery nozzle of the medicine delivery assembly by communicating the one or more control units with one or more first driving motors connected to the medicine delivery nozzle, and directing one or more three-dimensional rotational movements of the medicine delivery nozzle of the medicine delivery assembly by communicating the one or more control units with one or more second motors connected to the medicine delivery nozzle.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments. The drawings are not necessarily to scale. The drawings are merely schematic representations, not intended to portray specific parameters of the invention.

DETAILED DESCRIPTION

Aspects of the present invention provide a method for using an apparatus to deliver medicine and to wash, clean, and dry a region of a human body that may not otherwise be easily accessible (e.g., to the perianal region). The apparatus includes a toilet seat assembly and a medicine delivery assembly. In addition, the apparatus may include a drying nozzle assembly and/or a spraying nozzle assembly. The medicine delivery assembly may include one or more medicine storage cartridges and/or one or more medicine base units, each medicine base unit includes at least a cartridge unit and at least a cartridges slot, wherein the cartridge slot is adapted to match with a medicine storage cartridge. The medicine delivery assembly may include a medicine delivery nozzle, which can be coupled to a spraying nozzle assembly, or may be operated by itself with a medicine delivery nozzle. Finally, the medicine delivery assembly is controlled by one or more control units.

Figure 1:
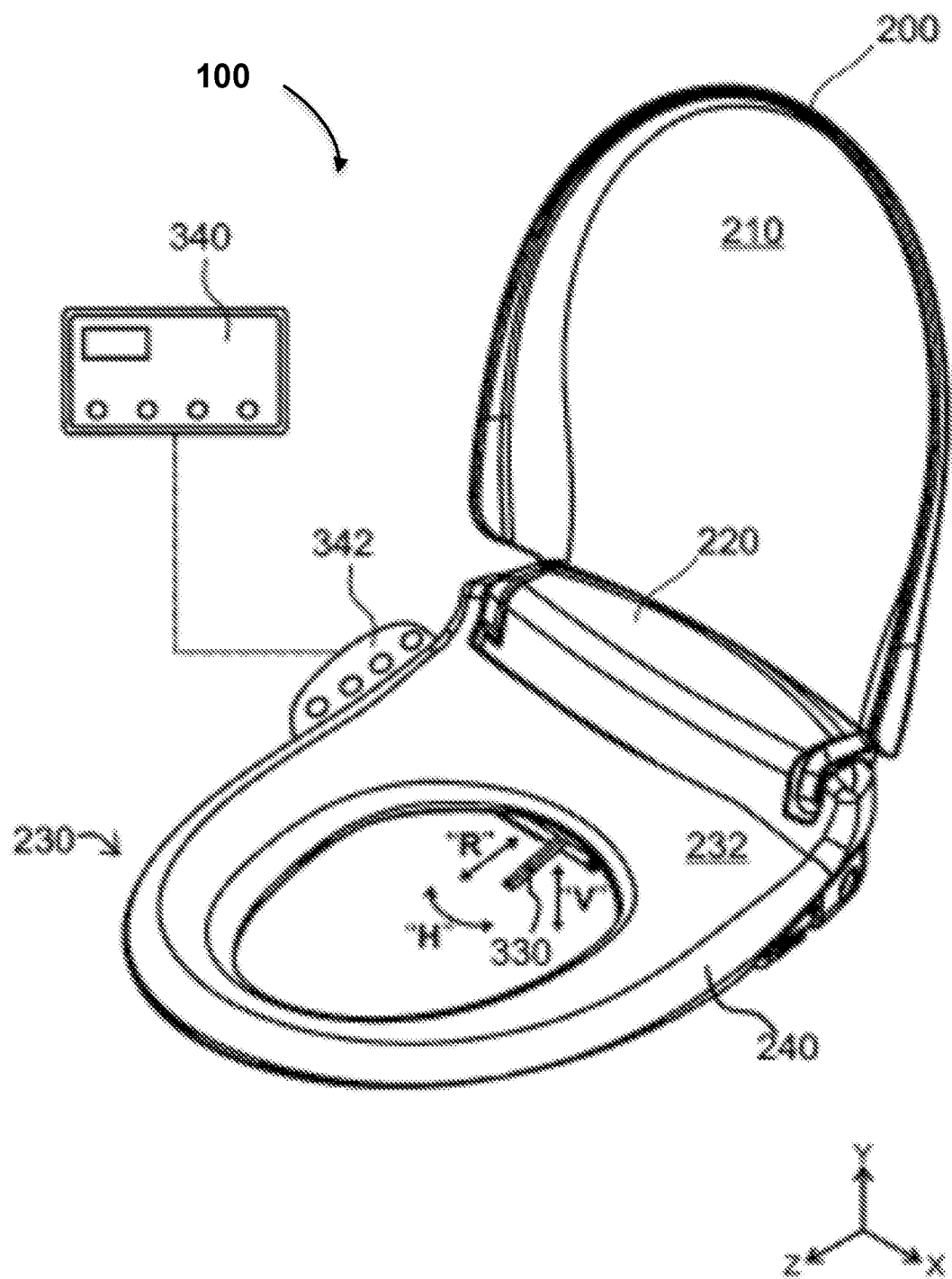
FIG. 1 is a perspective view of an example of a bidet seat system having a toilet seat assembly, a drying nozzle assembly, a spraying nozzle assembly, and a medicine delivery assembly according to embodiments of the invention.

FIG. 1 shows one example of a bidet seat and cover system, such as a bidet seat system 100. As shown in FIG. 1, the bidet seat system 100 may generally include a toilet seat assembly 200, a spraying nozzle assembly 300 having a spray nozzle unit 330, and one or more control units 340, 342. The bidet seat system 100 can be placed on top of a traditional toilet bowl with fitted sizes and shapes (oval or round). In one example, the toilet seat assembly 200 can be installed to a toilet system by removing any existing seat from a traditional toilet system and replacing a traditional seat with the bidet seat system 100. In another example, the bidet system 200 may have fastening elements (e.g., screws, bolts, velcro, etc.) in its base to be connected to a traditional toilet bowl.

As shown in FIG. 1, the toilet seat assembly 200 includes a seat cover 210, a base housing 220, a seat 230 and a base 240. The seat cover 210 is generally closed to cover the base 240. During operation or in idle position, the seat cover can be opened and positioned upward, such as being positioned against a water tank. The seat 230 includes a seat body 232 facing upward so that a human subject can sit thereon.

The base housing 220 and the base 240 are formed to connect the seat cover 210 and the seat 230 together, for example, using one or more hinges such that the seat cover 210 can be opened or closed against the seat 230. The housing 220 and the base 240 are used generally to house one or more assemblies (e.g., the spraying nozzle assembly 300, a drying nozzle assembly 600, and a medicine delivery assembly 400, etc.) therein. As shown in FIG. 1, the spray nozzle unit 330 is adapted to be retractable and can be positioned inside the base housing 220 and extended out in a direction "R" to move in three dimensional rotational direction and in a horizontal plane "H". The spray nozzle unit 330 positioned near the bottom of the seat body 232 can be adjusted to be retracted back into the base housing 220.

In one embodiment, the function and operation of the bidet system 100 is controlled by one or more control units, such as a control unit 342 positioned adjacent to one side of the bidet system 100, and a controlled unit 340, which can be positioned at a distance away from the bidet system in a wired or wireless fashion. In FIG. 1, two control units 340, 342 are configured, where the control unit 342 is positioned to be adjacent the seat body 232 to be closer for a user to control the movements of the spray nozzle unit 330 of the spraying nozzle assembly 300 as well as the temperature and pressure of the spraying liquid spraying from the spray nozzle unit 330. Alternatively, the control unit 340 may be a remote controlled unit being capable of communicating with the bidet seat system 100.

The remote control units 340, 342 are adapted to be communicating and directing one or more movements of the spraying nozzle unit 330. The spray nozzle unit 330 is adapted to jet a solution, such as water or any liquid, a cleaning solution, a barrier spray solution, a medicine-containing solution, and combinations thereof to a localized region (e.g., perianal region) of a human body private part. In one example, the spray nozzle unit 330 is adapted to move in a direction marked as "R" to be extended and retracted in and out. In another example, the spray nozzle unit 330 is adapted to move in a vertical direction marked as "V" to move up and down (e.g., in a Z-direction or a gravitational direction), particularly after the spray nozzle unit 330 has been extended and retracted out. In another example, the spray nozzle unit 330 is adapted to move in a horizontal direction marked as "H" to move left-right, particularly after the spray nozzle unit 330 are extended and retracted out.

The remote control units 340, 342 can cause the user to operate the operation button reliably. The remote control units can provide "hands-free" options, therefore avoiding some discomfort or embarrassment from the user. For example, control units 340 can be mounted on the wall adjacent to or far away from the toilet. The control unit 340 has a screen and a keyboard with pushbuttons for turning the water or air on and off, for controlling the air temperature, etc. The water flow level may be selected by appropriate command through the remote control unit. The remote control unit is used to transmit appliance control data to the bidet seat system 100. Inside the bidet seat system 100, a decoder decodes the transmitted data. When the data is decoded, the bidet seat system 100 responds to an appliance control signal suitable for controlling the spraying nozzle assembly 300 and other parts within the bidet seat system 100. As another example, control units 342 can be mounted on the base 240. It enables a user to directly control the bidet seat system 100.

Figure 2:
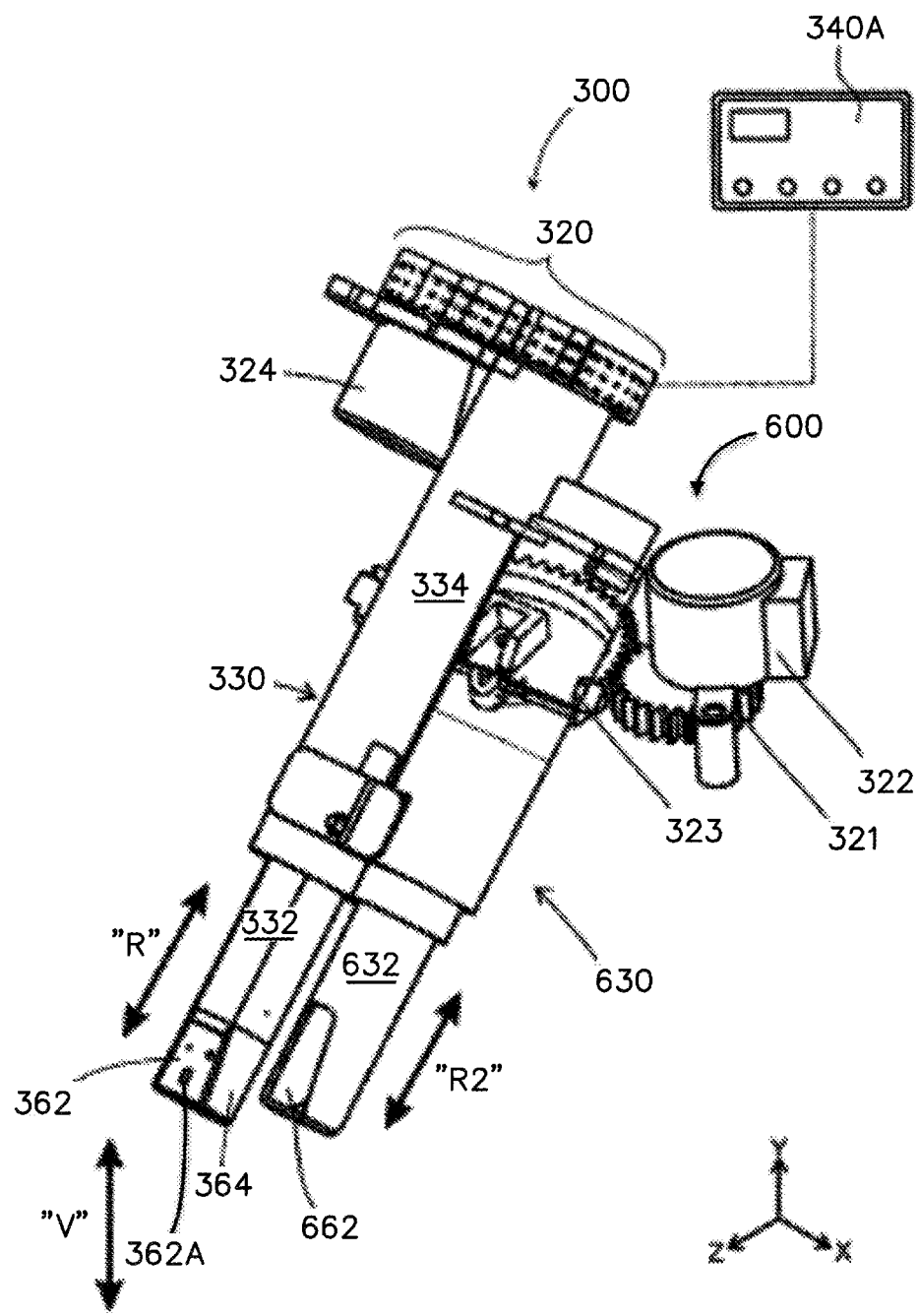
FIG. 2 illustrates one example of a bidet seat system having a drying nozzle assembly and a spraying nozzle assembly where their movements are controlled by a control unit connected thereto according to embodiments of the invention.

FIG. 2 shows one example of the spraying nozzle assembly 300 and the drying nozzle assembly 600, where their movements are controlled by a control unit 340A connected thereto. In one embodiment, the spraying nozzle assembly 300 includes a driving motor unit 320 to direct and drive the movements of the spray nozzle unit 330. The driving motor unit 320 is connected to a motor 324.

In another embodiment, the spray nozzle unit 330 includes one or more first spray nozzle body 332 and one or more second spray nozzle body 334, which are configured to function together and adapted to be retractable (as shown in a "R1" direction for extending and retracting movements) and movable in three-dimensional rotational motion, as driver by one or more driving motors (such as a driving motor 324, etc.) and steering gears (such as steering gears 321, 323, etc.) for delivering a solution therein.

Figure 4:
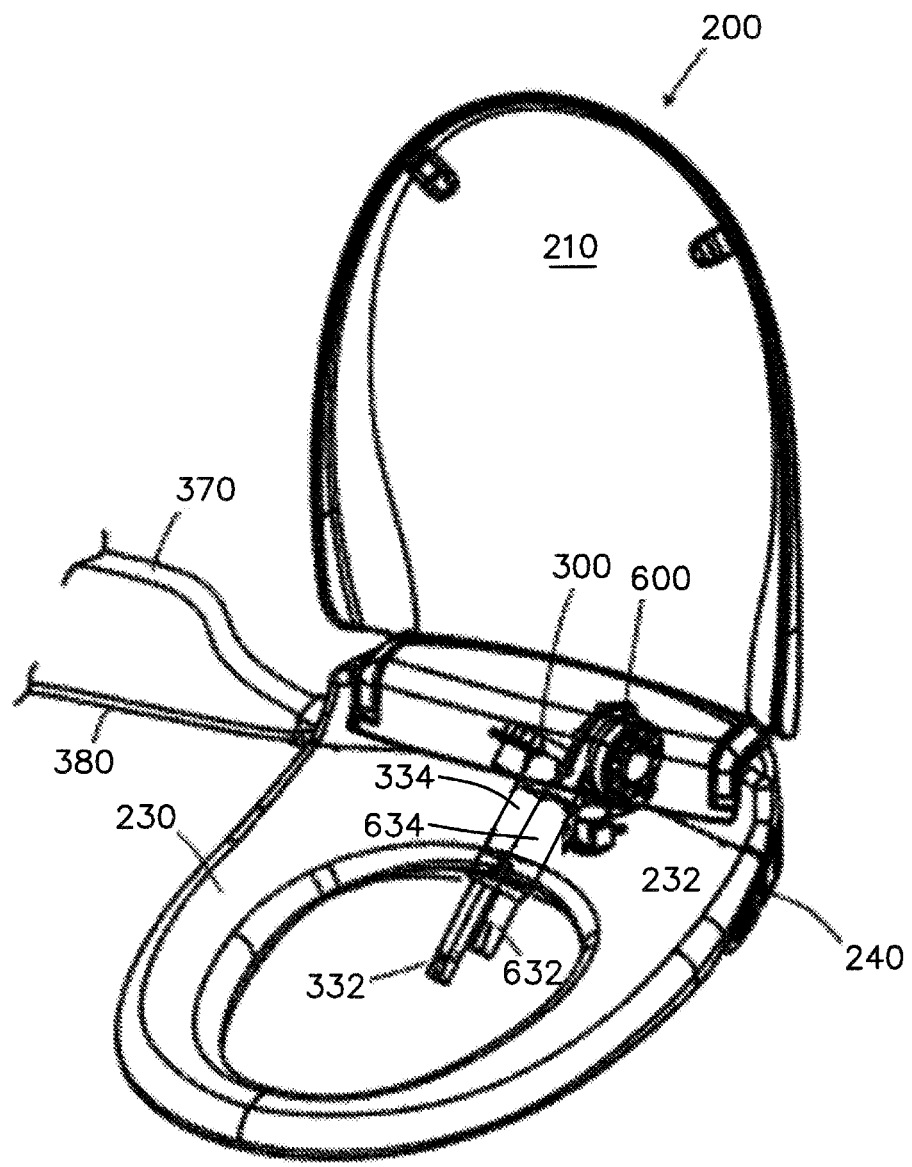
FIG. 4 shows another example of a bidet seat and cover system having two liquid lines connected to the spraying nozzle assembly according to embodiments of the invention.

Inside the first spray nozzle body 332 and the second spray nozzle body 334, there may be one, two or more spray nozzle channels, such as a first spray nozzle channel 362 and a second spray nozzle channels 364. Both of the first spray nozzle channel 362 and the second spray nozzle channels 364 are connected to the same or different liquid lines (such as liquid lines 370, 380 as shown in FIG. 4) for delivering one or more liquid solutions therein. Suitable solutions include water, a cleaning solution, a barrier spray solution, a medicine-containing solution, and combinations thereof. For example, medications, cleaning solutions, moisturizing creams, lotions, skin sealants, moisture barriers, skin protection paste, ointments, pastes or solutions of mineral oil, silicone fluids (e.g. dimethicone and cyclomethicone), petrolatum, cod liver oil, lanolin, zinc oxide, talc, calamine, kaolin, topical starch and allantoin, lotions, fluids medicaments, skin protection fluid, chemical suspensions, and/or a pharmaceutical formulation to a surface area of a human subject. For example, Desitin® ointment (Pfizer, Inc.) is probably the most common topical used in treating diaper rash and other rashes. It contains common barrier materials (zinc oxide and petrolatum) and additionally contains two common skin conditioning agents (cod liver oil and lanolin).

Also shown in FIG. 2 is the drying nozzle assembly 600, which includes a drying nozzle unit 630 having a retractable element 634 and a nozzle tip portion 632. A drying nozzle opening is positioned at the tip of the nozzle tip portion 632. The retractable element 634 and the nozzle tip portion 632 of the drying nozzle unit 630 are configured to be retractable (as shown in a "R2" direction) and movable in three-dimensional rotational motion, as driven by one or more driving motors (such as a driving motor 638, etc.) and steering gears (such as a steering gears 321, 323, etc.).

In one embodiment, the movements of the spraying nozzle unit 330 and the drying nozzle unit 630 may be driven by a separate set of motors and steering gears. In another embodiment, the movements of the spraying nozzle unit 330 and the drying nozzle unit 630 may be driven by a shared set or partially shared set of motors and steering gears. For example, as shown in FIG. 2, the driving motors 322, 324, may be coupled together by steering gears 321, 323 to function and drive coherently in order to coordinate and direct the movements of the spraying nozzle unit 330 and the drying nozzle unit 630.

The steering gears 321, 323 can rotate clockwise or counterclockwise. In one example, the driving motor unit 324 can be adapted to control the movements of the first spray nozzle body 332 and the second spray nozzle body 334 so that they are retractable, moving in a retractable direction, marked as "R1", to be extended and retracted in and out of the front end of the spray nozzle unit 330. In another example, the first spray nozzle body 332 and the second spray nozzle body 334 of the spraying nozzle unit 330 are configured to move in a vertical direction, marked as "V", to move up and down, particularly after the spraying nozzle unit 330 are extended and retracted out. In another example, the motor 324 can be adapted to control the movement of the nozzle tip portion 632 to be able to move in a retractable direction, marked as "R2", to be extended and retracted in and out of the front end of the drying nozzle unit 630.

Figure 3A:
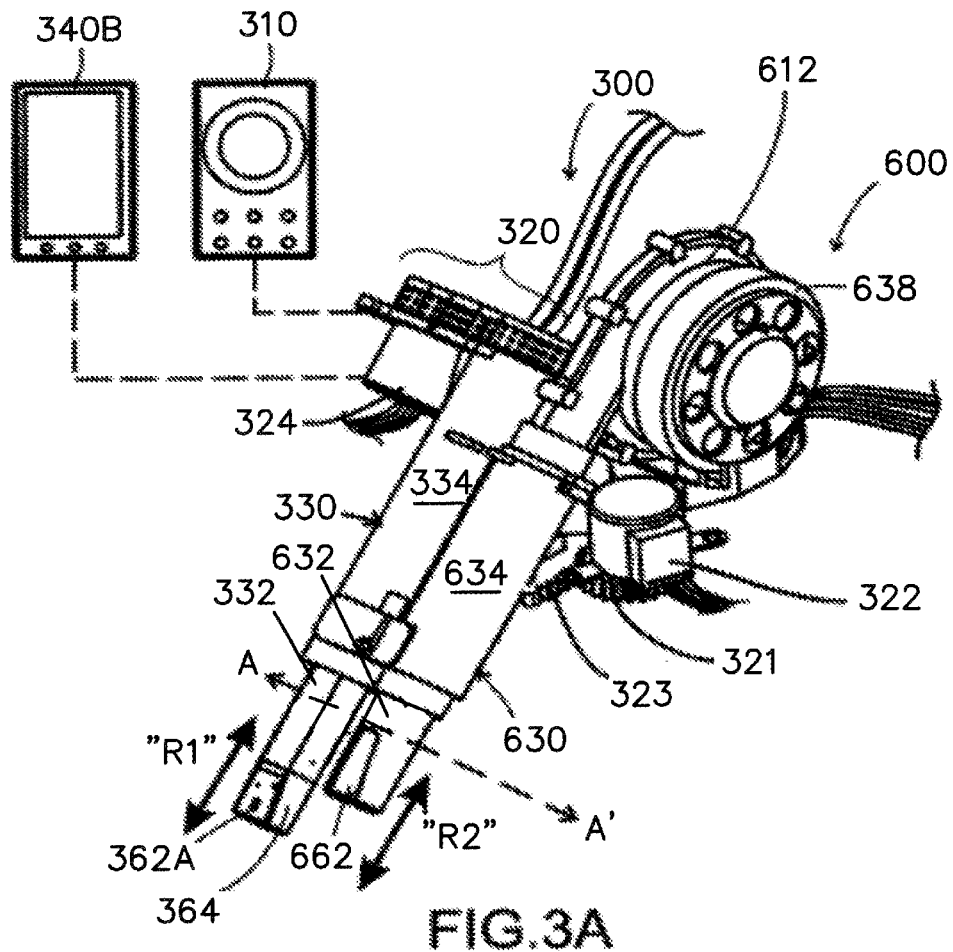
FIG. 3A illustrates another example of a bidet seat system having a drying nozzle assembly and a spraying nozzle assembly, and one or more remote control units according to embodiments of the invention.

FIG. 3A illustrates another example of the bidet seat system 100 having the spraying nozzle assembly 300, the drying nozzle assembly 600, and one or more control units 310, 340. The bidet seat system includes one or more motors 322, 324 that are coupled to function coherently by one or more gears 321,323.

The control units 310, 340 can be used for remotely controlling the spray nozzle assembly 300 and the drying nozzle assembly 600. In one embodiment, the control unit 340 may include touch screen display that can detect one or more finger contacts. In other embodiments, the control units 310, 340 may include control buttons, a joystick, a slider, a remote control unit, a hand-held control unit, a touch screen control unit, a joystick-type control unit, a steering-wheel type control unit, a built-in control unit being secured adjacent the toilet seat assembly, any other control device now known or later developed, and/or combinations. The remote control units 310, 340 allow for the operation of devices that are out of convenient reach for direct operation of controls. The control units 310, 340 can receive an input from a user of the bidet seat system 100 and transmit the user input to the responsible parts and components for the movements of the spray nozzle assembly 300 and the drying nozzle assembly 600.

Figure 3B:
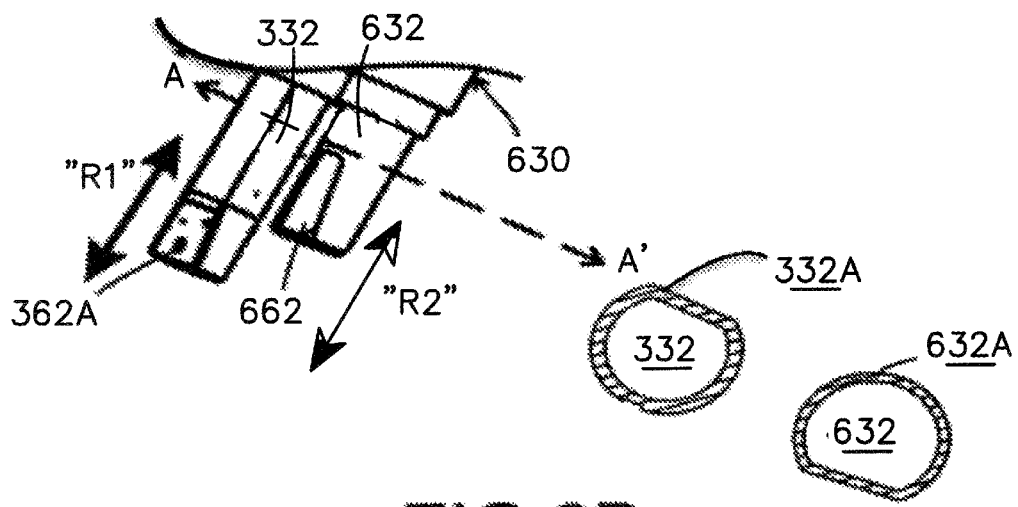
FIG. 3B is a partially enlarged view of a nozzle body and a nozzle jet head opening of the spraying nozzle assembly and a drying nozzle opening of the drying nozzle assembly of FIG. 3A and a cross-sectional view of the nozzle body of the spraying nozzle assembly and a nozzle tip portion of the drying nozzle assembly according to embodiments of the invention.

FIG. 3B is a partially enlarged view of the first spray nozzle body 332 and the nozzle jet head opening 362A of the spraying nozzle assembly 330 and the drying nozzle opening 662 of the drying nozzle assembly 630 of FIG. 3A and a cross-sectional view of the first spray nozzle body 332 of the spraying nozzle assembly 330 and the nozzle tip portion 662 of the drying nozzle assembly 630, cutting along the line A-A' according to embodiments of the invention.

FIG. 4 shows another example of the toilet seat assembly 200. In one embodiment, the toilet seat assembly 200 is connected with the liquid lines 370, 380 for a source of hot water and a source of cold water, and for a cleaner solution or medicine-containing solution. In another embodiment, the toilet seat assembly 200 is connected with the liquid lines 370, 380 and capable of water jetting or delivering a medicine-containing solution.

Figure 5A:
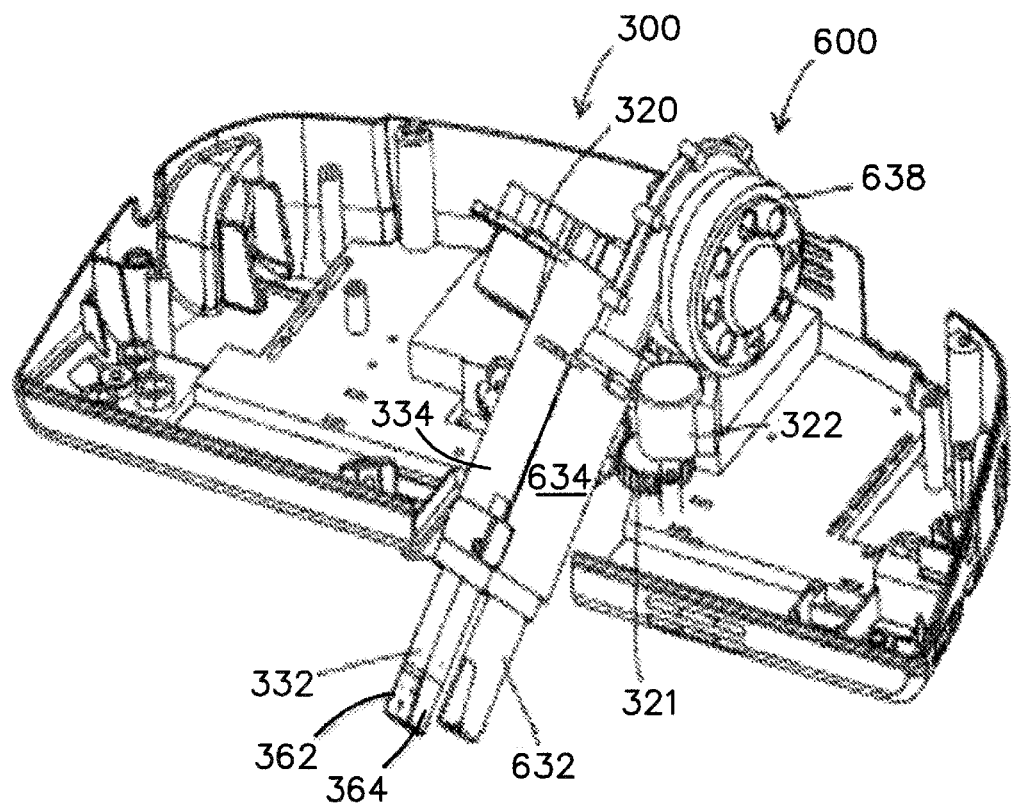
FIG. 5A is an internal perspective view of one example of a base housing of a toilet seat assembly to illustrate inside views of a spray nozzle assembly and a dry nozzle assembly according to embodiments of the invention.
Figures 5B, 5C:
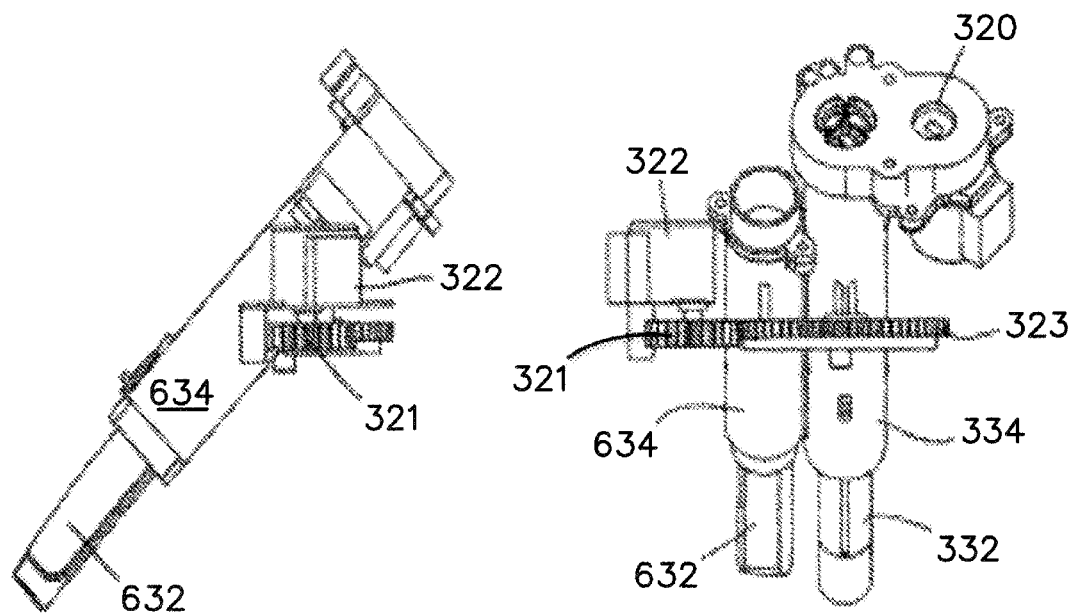
FIG. 5B is a partially enlarged side view of the drying nozzle assembly of FIG. 5A according to embodiments of the invention.
FIG. 5C is a partially enlarged bottom view of the spray nozzle assembly and the drying nozzle assembly of FIG. 5A according to embodiments of the invention.

FIG. 5A shows an internal perspective view of the base housing 210 of the toilet seat assembly 200 to illustrate inside views of the spray nozzle assembly 300 and the dry nozzle assembly 600. The spraying nozzle unit 330 may include the first spray nozzle body 332, the second spray nozzle body 334, whose movements are driven by the driving motor units 320, 322. FIG. 5B is a partially enlarged side view of the drying nozzle assembly 600 of FIG. 5A and FIG. 5C is a partially enlarged bottom view of the spray nozzle assembly 300 and the drying nozzle assembly 600 of FIG. 5A. As shown in FIGS. 5A-5C, the driving motor units 320, 322 may be coupled together by one or more steering gears 321, 323 in order to coordinate and direct the movements of the spray nozzle assembly 300 and the drying nozzle assembly 600.

Figure 6:
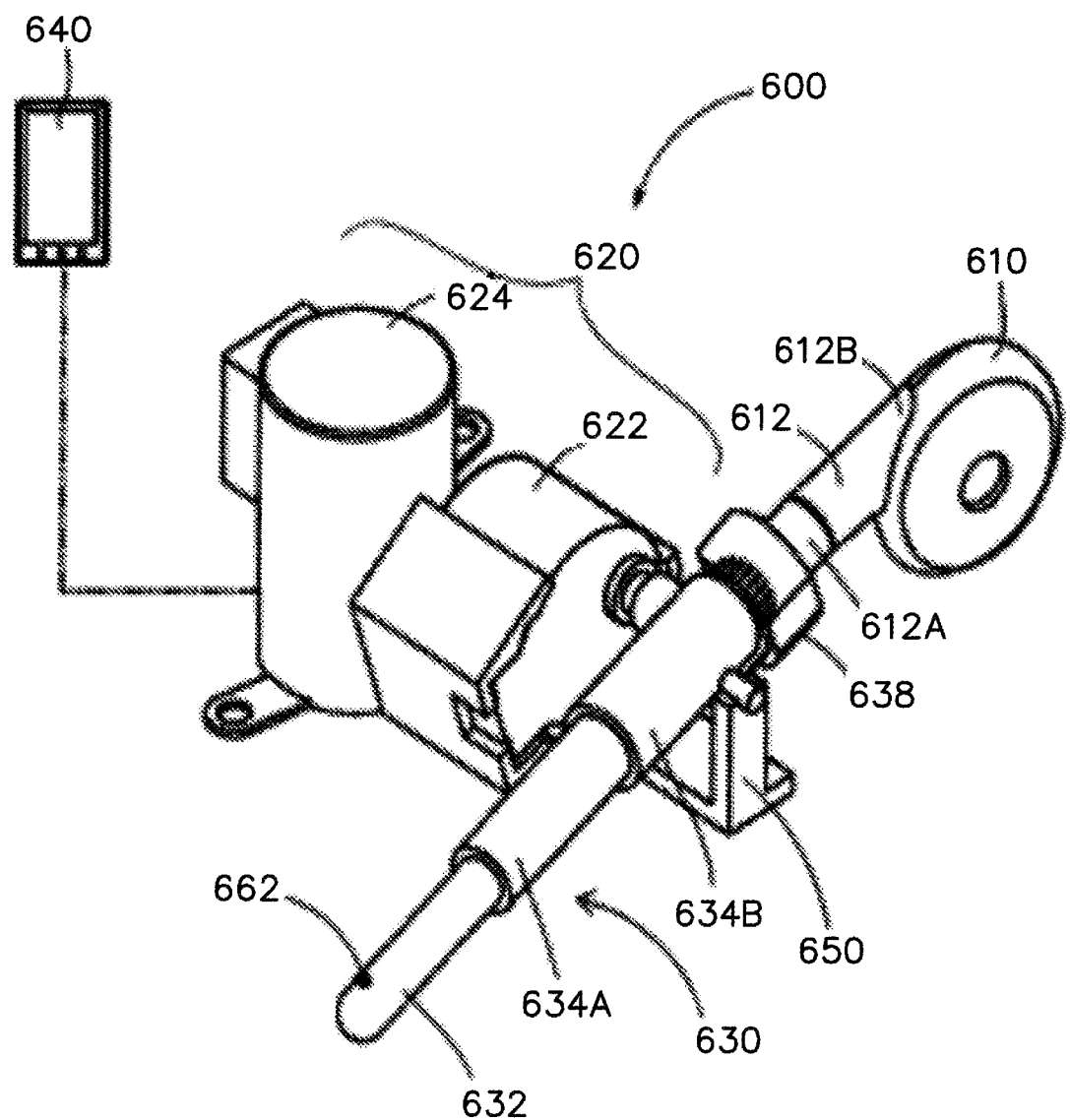
FIG. 6 illustrates one example of a dry nozzle assembly being adapted to communicate with a remote control unit according to embodiments of the invention.

FIG. 6 illustrates the movements of the drying nozzle assembly 600 as driven by one or more motors, such as a driving motor assembly 620 having driving motors 622, 624, as connected and coupled by a connector base 650. The driving motors 622, 624 can be controlled by a control unit 640 (via wired or wireless connection) in order to coordinate and direct the movements of the drying nozzle assembly 600.

In one embodiment, the drying nozzle unit 630 includes a fan 610, one or more air channels 612, 612A, 612B, retractable elements 634, 634A, 634B, 634C, and a nozzle tip portion 632, with the drying nozzle opening 662 located at the tip. The drying nozzle unit 630 may be able to deliver air with the use of a high output power fan, such as the fan 610. In one embodiment, the fan 610 of the drying nozzle assembly 600 is adapted to blow air at an adjustable speed. In another aspect, the fan 610 of the drying nozzle assembly 600 is adapted to blow air at an adjustable temperature.

Figure 7:
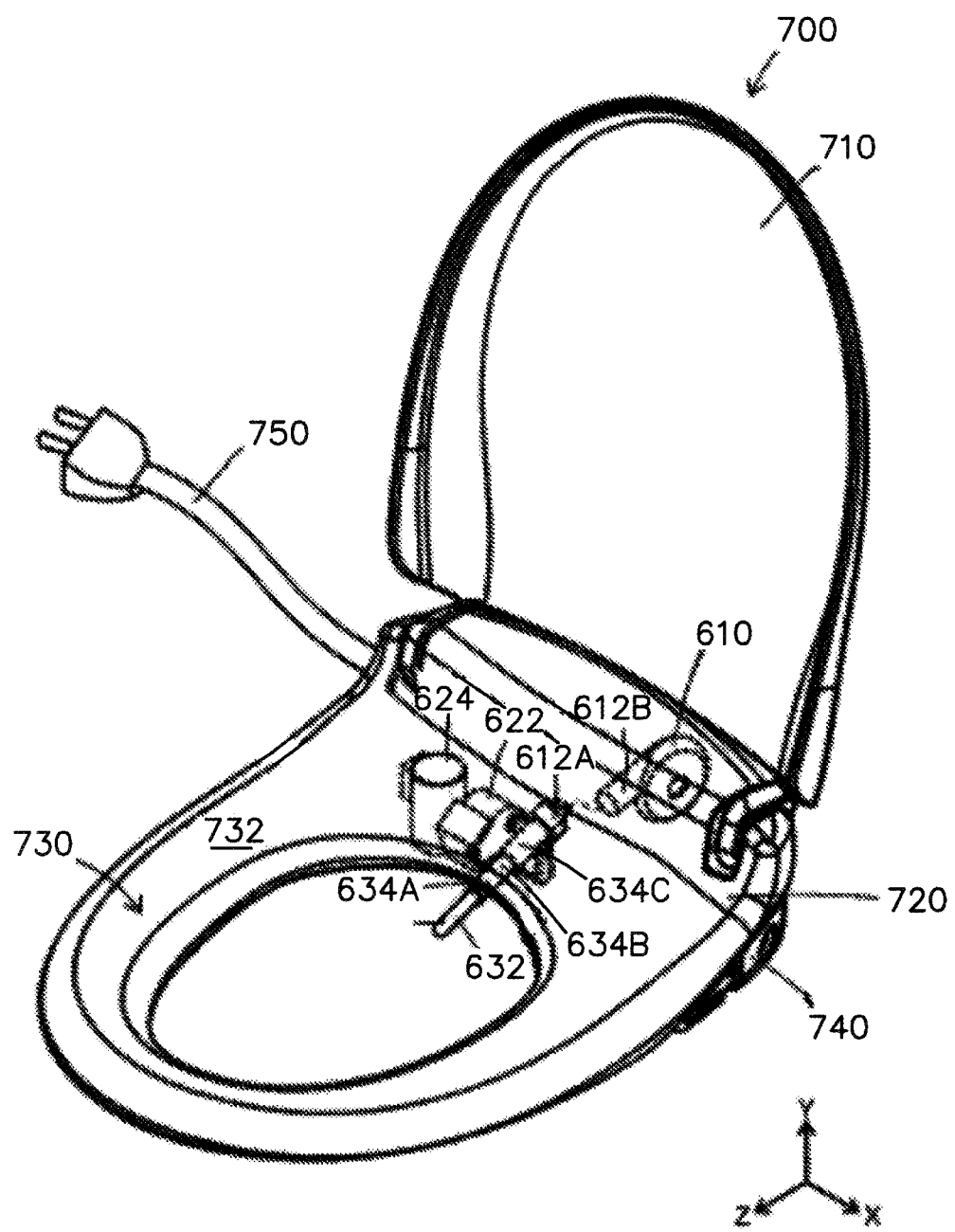
FIG. 7 is an internal perspective view of one example of a base housing of a bidet seat and cover system to illustrate the inside views of a dry nozzle assembly according to embodiments of the invention.

FIG. 7 is an internal perspective view of a base housing 720 of a toilet seat assembly 700 to show the inside views of the drying nozzle assembly 600. The toilet seat assembly 700 includes a seat cover 710, the base housing 720, a seat 730, a seat body 732, a base 740, and an electric wire 750. The toilet seat assembly 700 is connected, via the electric wire 750, to an electric outlet to provide electric driving power to various motors and fans within the toilet seat assembly 700.

Figure 8:
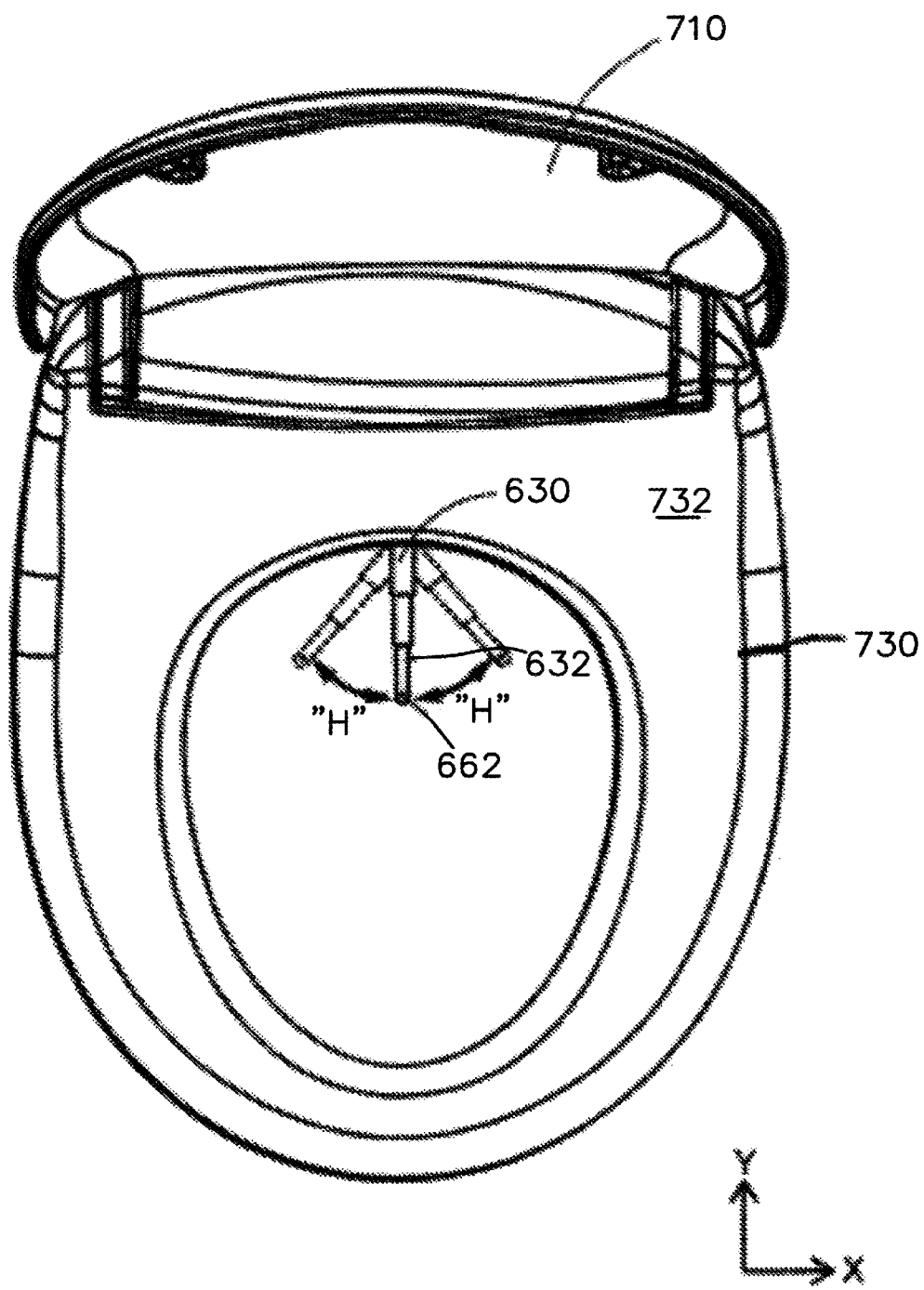
FIG. 8 is a top view of the bidet seat and cover of FIG. 7, showing the three-dimensional rotational movements of a drying nozzle assembly according to embodiments of the invention.

FIG. 8 shows a top view of the drying nozzle unit 630 stored inside the seat body 730 within the seat 730. Under the control of a user, the drying nozzle assembly 630 may extend the nozzle tip portion 632 out so as to blow air out of the drying nozzle opening 662 and dry an area or a region of a body part of a human subject. In addition to being retractable, the drying nozzle unit 630 is adapted to move in three-dimensional direction, vertically, horizontally, and circularly (as marked in an arrowed direction "H" (e.g., circular, or rotational, in three-dimensional, etc.) so as to be able to reach to a localized area near a region of a human body that needs to be dried.

Figure 9:
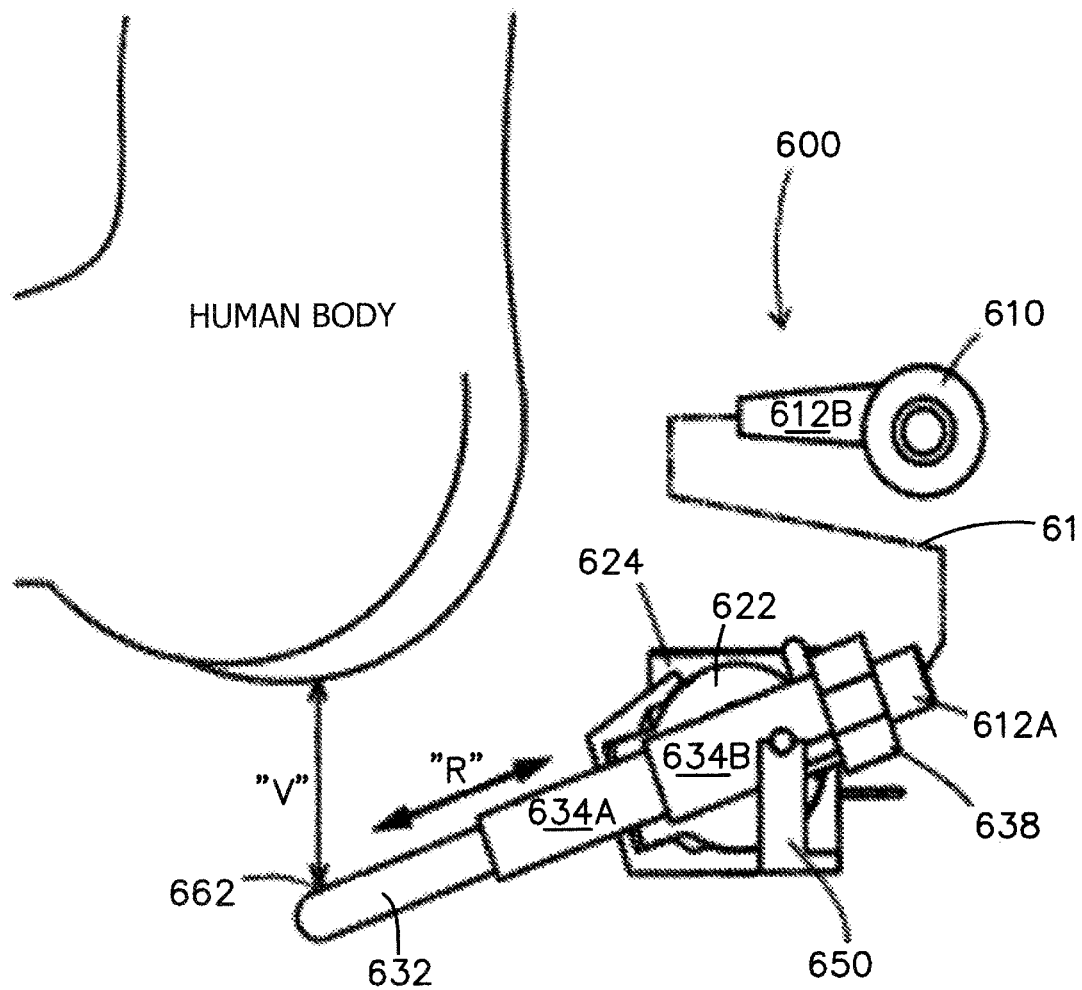
FIG. 9 is a side view showing one example of a drying nozzle assembly according to embodiments of the invention.

FIG. 9 is a side view showing a human subject using the drying nozzle assembly 600 according to embodiments of the invention. In one example, driving motors 622, 624 can be adapted to control the movements of the nozzle tip portion 632 to be able to move in a retractable direction, marked as "R", to be extended and retracted in and out of the front end of the drying nozzle assembly 600. In another example, the drying nozzle assembly 600 are able to move in a vertical direction, marked as "V", to move up and down, particularly after the drying nozzle assembly 600 is extended and retracted out.

Figure 10A:
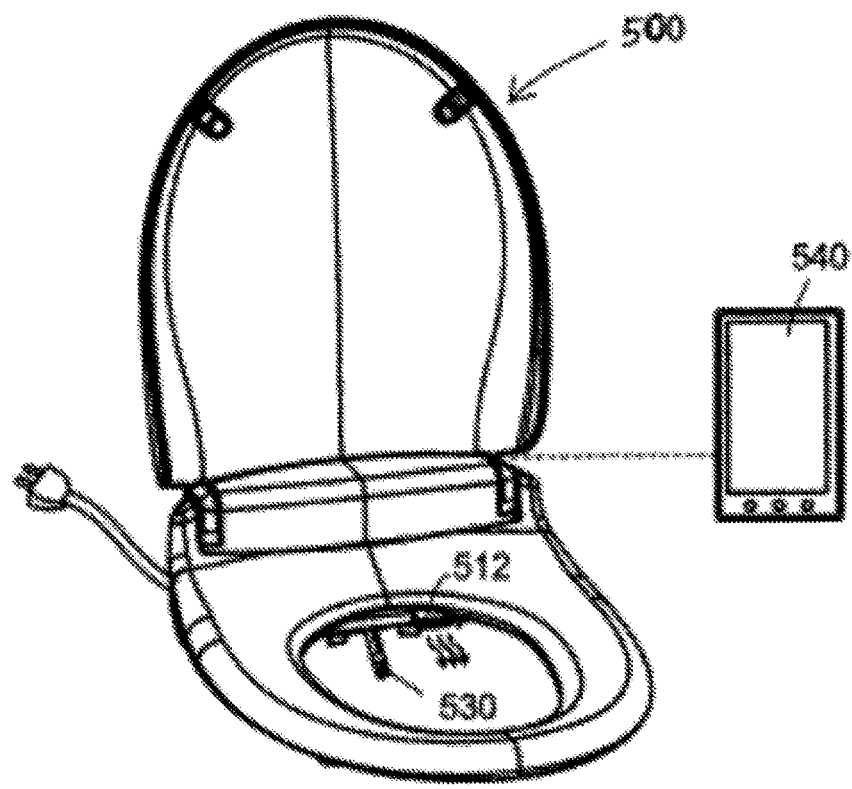
FIG. 10A is a perspective view of a prior-art conventional bidet seat system having a bidet toilet seat, a prior-art air vent, and a prior-art actable-only spray nozzle mechanism.
Figure 10B:
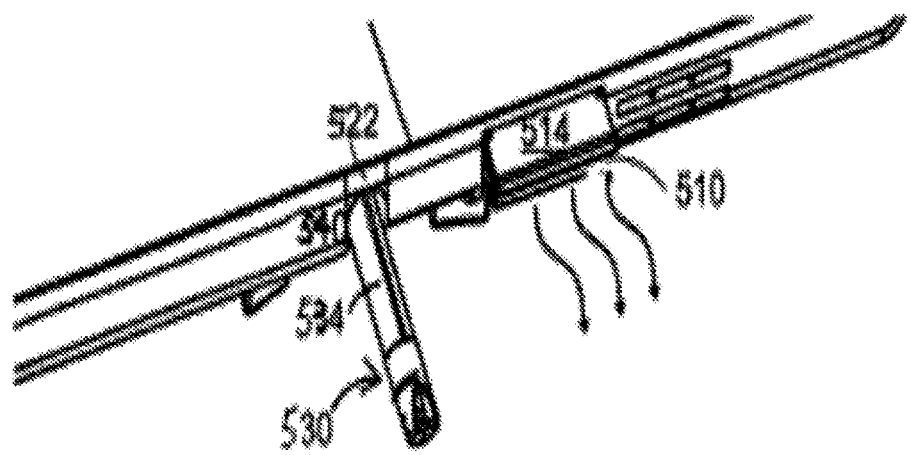
FIG. 10B is a partially enlarged view of a prior-art air vent and the prior-art retractable-only spray nozzle mechanism of FIG. 1A.

FIG. 10A is a perspective view of a prior-art conventional bidet seat system having a bidet toilet seat assembly 500, an air vent 512, and a spray nozzle mechanism 530. FIG. 10B is a partially enlarged view of the air vent 512 and the spray nozzle mechanism 530 of FIG. 10A. The air vent 512 generally includes a fan cover 514 and a plurality of leaves 510 to direct the direction of air flow (the leaves are used to direct air flow, similar to leaves on a small single-room air conditioner). The spraying nozzle mechanism 530 may include a cut-out 522 near a covering 540, where a spray nozzle 534 can extended out. The angles and movements of the spraying nozzle mechanism 530 and the air vent 512 are limited and usually are extended out downward and cannot be controlled to a desired area of a human body. They cannot be extended or retracted, in combination with raising up or lowering the angle to be near a region of the body of a user.

Figure 11:
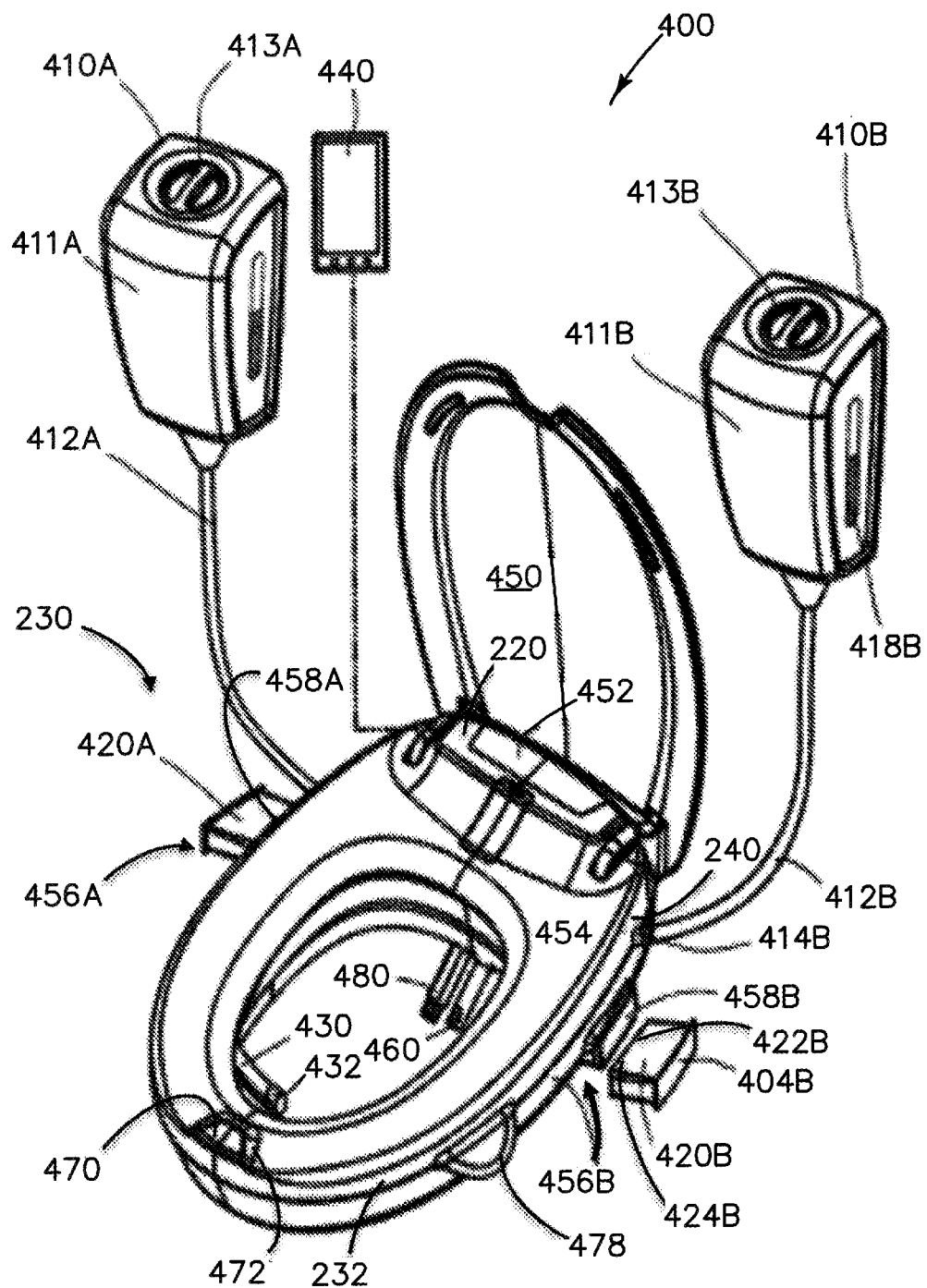
FIG. 11 shows one example of a medicine delivery assembly in conjunction with a spraying nozzle assembly and a drying nozzle assembly as controlled by a control unit remotely according to embodiments of the invention.
Figure 12:
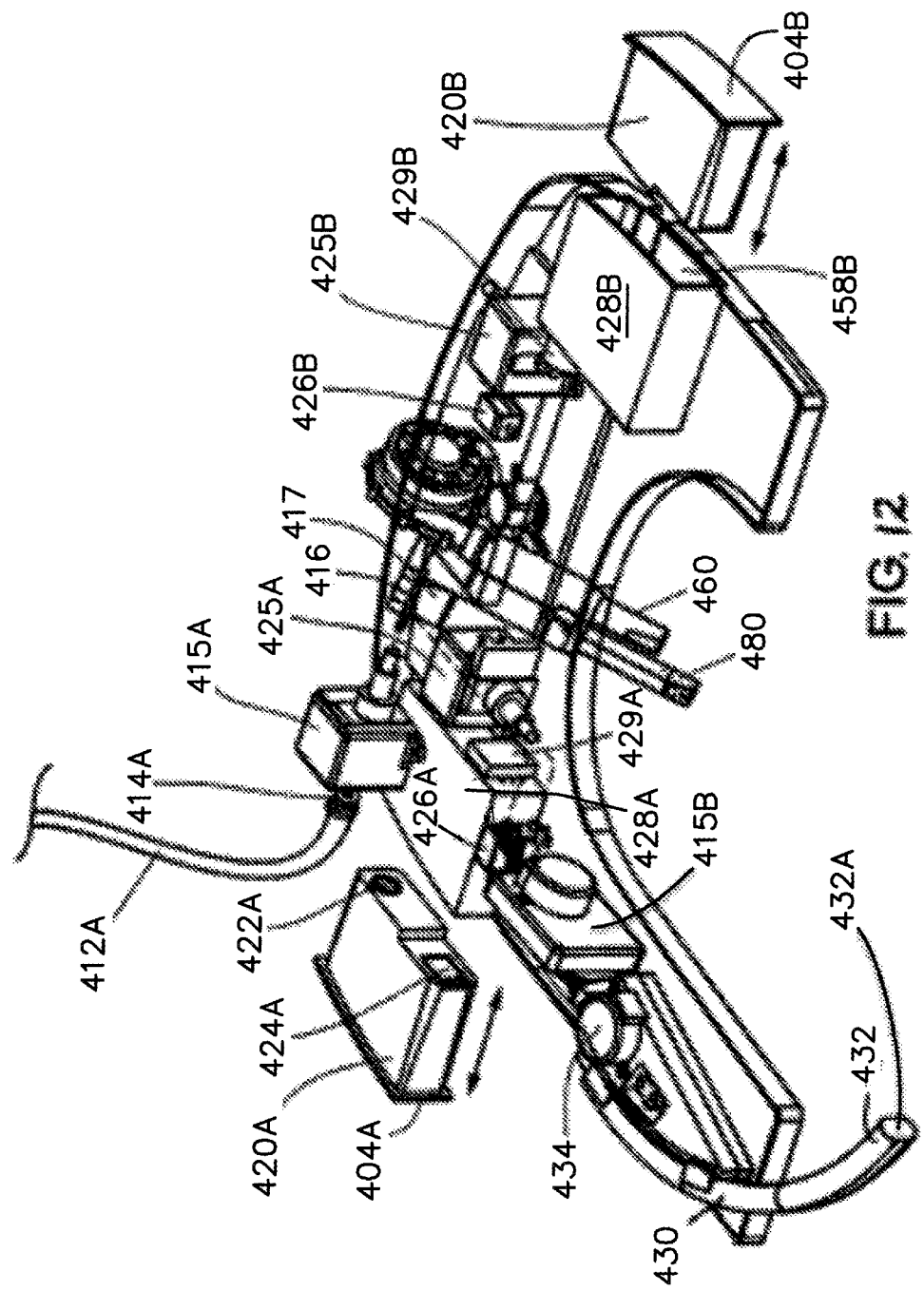
FIG. 12 is an internal perspective view of another example of a base housing of a bidet seat and cover system to illustrate interior views of a spraying nozzle assembly, a drying nozzle assembly, and a medicine delivery assembly, showing more than one suitable medicine base units, medicine storage cartridges, and a medicine delivery nozzle according to embodiments of the invention.
Figure 13:
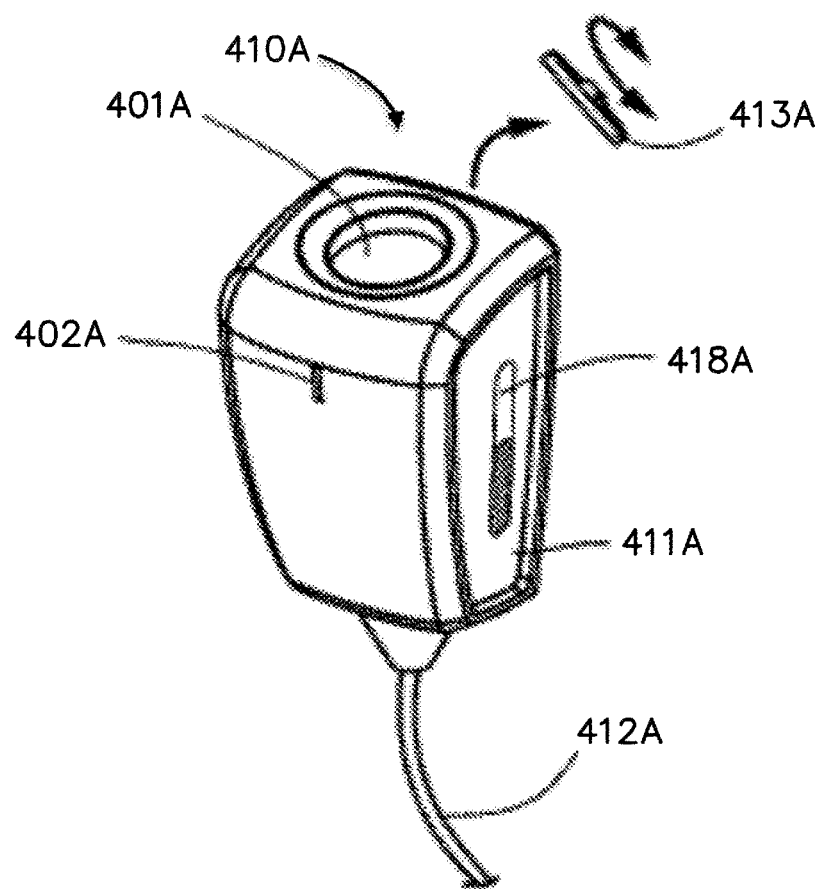
FIG. 13 illustrates one example of a medicine storage assembly according to embodiments of the invention.
Figure 14:
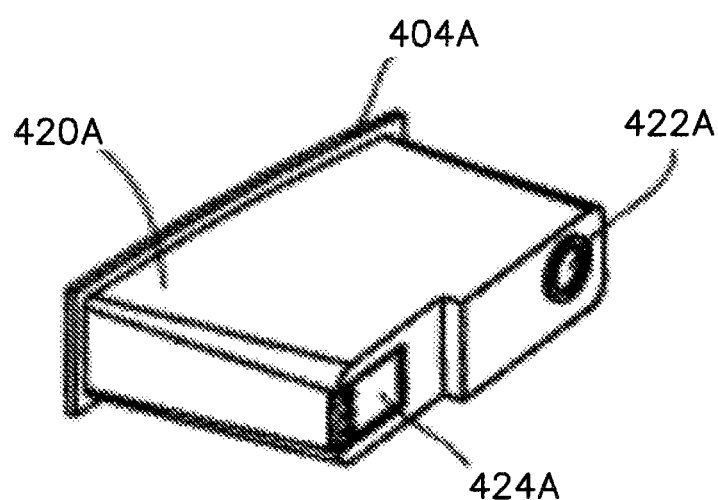
FIG. 14 illustrates one example of a medicine storage cartridge of a medicine base unit according to embodiments of the invention.
Figure 15A:
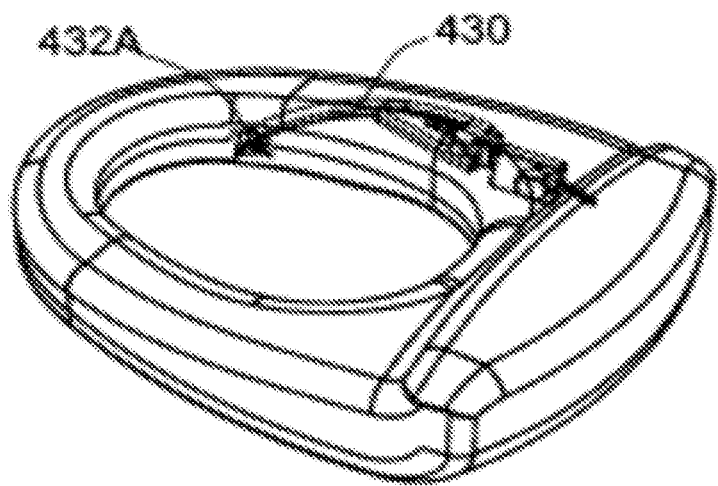
FIG. 15A is an internal perspective view of a medicine delivery assembly, showing one example of a medicine delivery nozzle the according to embodiments of the invention.

FIG. 11 shows one example of a medicine delivery assembly 400 in conjunction with a spraying nozzle assembly 480 and a drying nozzle unit 460 as controlled by a control unit 440 remotely according to embodiments of the invention. In one embodiment, the medicine delivery assembly 400 may include one or more medicine storage assemblies 410A, 410B for delivering a solution, such as a medicine-containing solution (e.g., zinc oxide, menthol-containing solutions, silicone fluids, dimethicone and cyclomethicone, petrolatum, cod liver oil, lanolin, zinc oxide, talc, calamine, kaolin, topical starch and allantoin, lotions, fluids medicaments, skin protection fluid, etc.) The medicine storage assemblies 410A, 410B may each include a medicine storage tank 411A, 411B, adapted for storing a medicine-containing solution, a tank cover 413A, 413B, a tubing 412A, 412B, and a pipe orifice 414A, 414B connected to the base 240 to go to the inside of the base housing 220.

In another embodiment, the medicine delivery assembly 400 can include one or more medicine storage cartridges, such as medicine storage cartridges 420A, 420B, and the medicine delivery assembly 400 is adapted to deliver one or more medicine-containing solutions that are stored at the medicine storage cartridges 420A, 420B. Once medicine-containing solution within the medicine storage cartridges 420A, 420B is low or empty, they can be easily replaced with a new set of matching medicine storage cartridges 420A, 420B.

In still another embodiment, the medicine delivery assembly 400 includes one or more medicine base units, such as a right medicine base unit 456A and/or a left medicine base unit 456B, etc. Each medicine base unit 456A, 456B includes at least a cartridge unit 428A, 428B, and at least a cartridges slot 458A, 458B, where each of the cartridge slot 458A, 458B is adapted to match with a medicine storage cartridge, such as medicine storage cartridge 420A, 420B.

In one aspect, each of the medicine storage cartridge 420A, 420B includes a cartridge cover 404A, 404B, a medicine inlet 422A, 422B being connected to a medicine storage assembly (such as the medicine storage assembly 410A, 410B or any other suitable medicine storage assembly, positioned within the base housing 220), and a sensor 429A, 429B for matching and identifying a medicine solution stored within the medicine storage assembly.

FIG. 13 shows one example of the medicine storage assembly 410. The tank cover 413B of the medicine storage assembly 410A can be opened and closed by clockwise or counterclockwise movements. The medicine storage tank 411A is adapted for storing a medicine-containing solution. In one example, the tubing 412A is connected to the medicine inlet 422A of the medicine storage cartridge 420A. In another example, the medicine storage assembly 410A, 410B further includes a medicine storage element 402A, 402B, which is adapted to store one or more medicines to be mixed with water to form into the medicine-containing solution.

In another example, the medicine storage assembly 410A, 410B further includes a liquid solution indicator 418A, 418B adapted to indicate the content level of the medicine-containing solution within the medicine storage tank 411A, 411B. Further, the medicine storage assembly 410A, 410B may also include a pressurized pump 415A, 415B adapted to pump and deliver the medicine-containing solution from the medicine storage tank 411A, 411B into the toilet seat assembly 200.

FIG. 14 illustrates details of the medicine storage cartridge 420A, which is coupled to a sensor 424A to indicate the current status of a medicine-containing solution stored therein. The medicine storage cartridges 420A, 420B can be pulled out from the cartridge slot 458B for adding or changing medicines.

Referring back to FIG. 12, which shows an internal perspective view of another example of the base housing 220 of the bidet seat and cover system 100 to illustrate interior views of the spraying nozzle assembly 300, the drying nozzle unit 460, and the medicine delivery assembly 400, showing more than one suitable medicine base units (such as the right medicine base unit 456A and the left medicine base unit 456B), more than one medicine storage cartridges 420A, 420B, and a medicine delivery nozzle 430 according to embodiments of the invention.

As shown in FIG. 12, the medicine delivery assembly 400 can include one or more driving motors 426A, 426B, one or more steering gears 416, and a medicine delivery nozzle 430 having a nozzle body 432 that is adapted to be retractable and movable rotationally and vertically in three-dimensional direction. In one embodiment, the medicine delivery nozzle 430 is adapted to deliver one or more medicine-containing solutions to the region of the human body.

In one aspect, the medicine delivery nozzle 430 includes an atomizer nozzle head 432A adapted to atomize a medicine-containing solution to achieve a consistency that can be applied over a distance and deliver a stream of the medicine-containing solution to a user. In another aspect, the medicine delivery nozzle 430 is adapted to deliver the medicine-containing solutions across a space to a perianal region of a user. In still another aspect, the medicine delivery assembly 400 further includes a pressurized pump 425A, 425B adapted to pump and deliver the medicine-containing solution from the medicine inlet 422A, 422B of the medicine storage cartridge 420A, 420B.

In still another embodiment, the spraying nozzle assembly 480 and the medicine delivery nozzle 430 of the medicine delivery assembly 400 may be adapted to be able to move similarly in three-dimensional dynamic movements, but be separated physically from each other to work together in spraying a solution and delivering a medicine-containing solution, respectively. FIG. 15A is an internal perspective view of the medicine delivery assembly 400, showing one example of the medicine delivery nozzle 430 that works independently in delivering a medicine-containing solution without going through the spraying nozzle assembly 400 positioned near base housing 220.

Figure 15B:
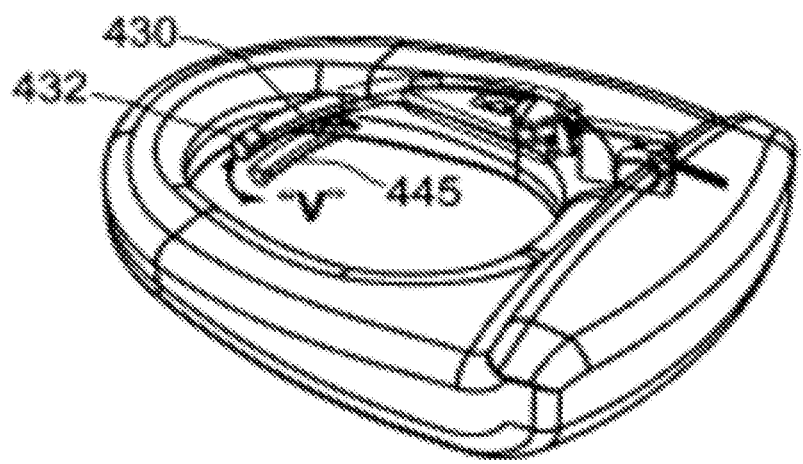
FIG. 15B illustrates vertical movements of the medicine delivery nozzle of the medicine delivery assembly of FIG. 15A.

FIG. 15B illustrates vertical movements of the medicine delivery nozzle 430 of the medicine delivery assembly 400 of FIG. 15A. The medicine delivery nozzle 430 is adapted to move in a vertical and/or rotational direction, marked as "V", to move up and down, particularly after the medicine delivery nozzle 430 are extended out, not retracted.

Figure 15C:
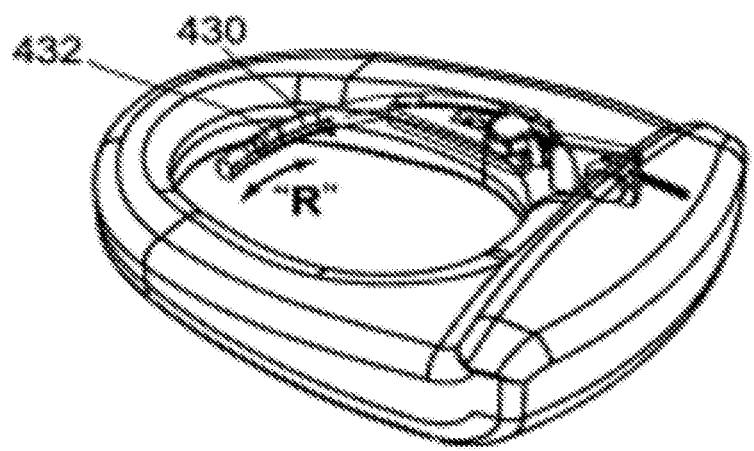
FIG. 15C illustrates retracting and extending movements of the medicine delivery nozzle of the medicine delivery assembly of FIG. 15A.

FIG. 15C illustrates the retracting and extending movements of the medicine delivery nozzle 430 of the medicine delivery assembly 400 of FIG. 15A. The medicine delivery nozzle 430 is adapted to move in a retractable direction, marked as "R", to be retracted in and extended out of the front end of the medicine delivery nozzle 430.

In one embodiment, the medicine delivery assembly 400 may be adapted to couple to and function together to deliver a medicine-containing solution to the one or more spray nozzle channels of the spraying nozzle assembly 300 and/or the spraying nozzle assembly 480. In one aspect, the spray nozzle channels of the spraying nozzle assembly 300, 480 includes the nozzle jet head opening 362A adapted to deliver any suitable solution at high speed. Suitable solution may be selected form the group consisting of water, a cleaning solution, a barrier spray solution, a medicine-containing solution, and combinations thereof.

Figure 16:
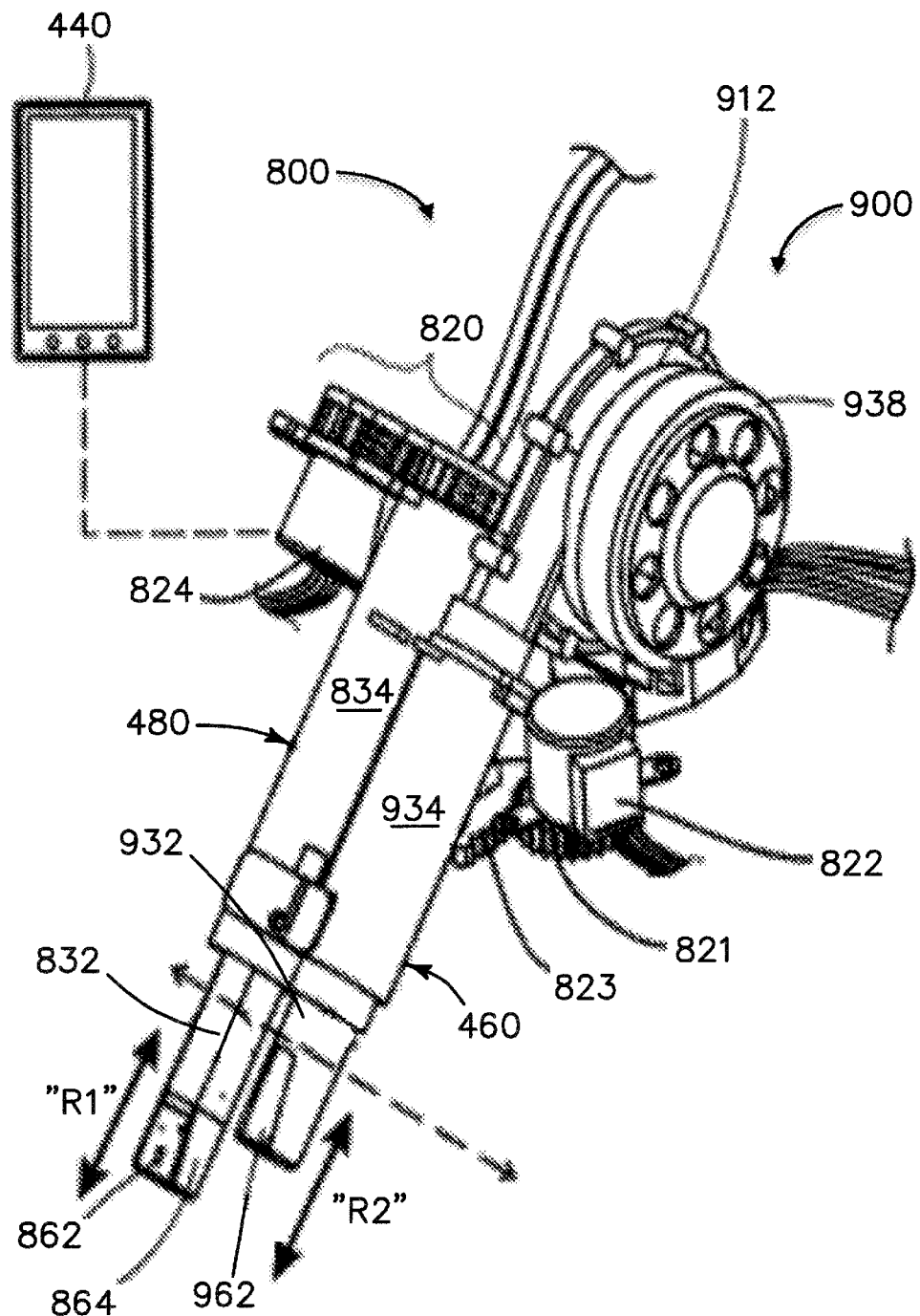
FIG. 16 illustrates another example of a spray nozzle assembly, a drying nozzle assembly as controlled according to embodiments of the invention.

FIG. 16 illustrates another example of a spraying nozzle assembly 800, a drying nozzle assembly 900 as controlled a control unit 440. The spraying nozzle assembly 800 includes a nozzle body 834 and a nozzle tip portion 832, and their movements are driven by one or more driving motor units 820 with one or more driving motors 822, 824, which are coupled to steering gears 821, 823 to function together. Two nozzle channels with nozzle tip openings 862, 864 are configured inside the nozzle body 834 for separately delivering water and a cleaning solution in each nozzle channel. Alternatively, the two nozzle channels may be configured to deliver water and a medicine-containing solution each.

The drying nozzle assembly 900 includes a fan 938, one or air channels 912 connected to the fan 938, one or more drying nozzle units 460 connected to the one or more air channels 912, and one or more driving motor units 820 with driving motor 822, 824, which are shared with the spraying nozzle assembly 800 so that the spraying nozzle assembly 800 and the drying nozzle assembly 900 can be coupled to move together. In one aspect, the one or more driving motor units 820 of the medicine delivery assembly 900 includes one or more steering gears, a first driving motor being connected to the one or more drying nozzle units and the one or more steering gears, wherein the first driving motor is adapted to move the one or more drying nozzle units in retracting-and-extending motion. In another aspect, the one or more driving motor units of the medicine delivery assembly further includes a second driving motor being connected to the one or more drying nozzle units and the one or more steering gears, wherein the second driving motor is adapted to move the one or more drying nozzle units in three-dimensional circular rotational motion.

Another embodiment of the invention provides one or more control units connected to the toilet seat assembly and the medicine delivery assembly, where the control units are adapted to receive a user input and, based on the user input, to direct movements of one or more motors and adjust the positions of one or more nozzles within the toilet seat assembly and the medicine delivery assembly.

Figure 17:
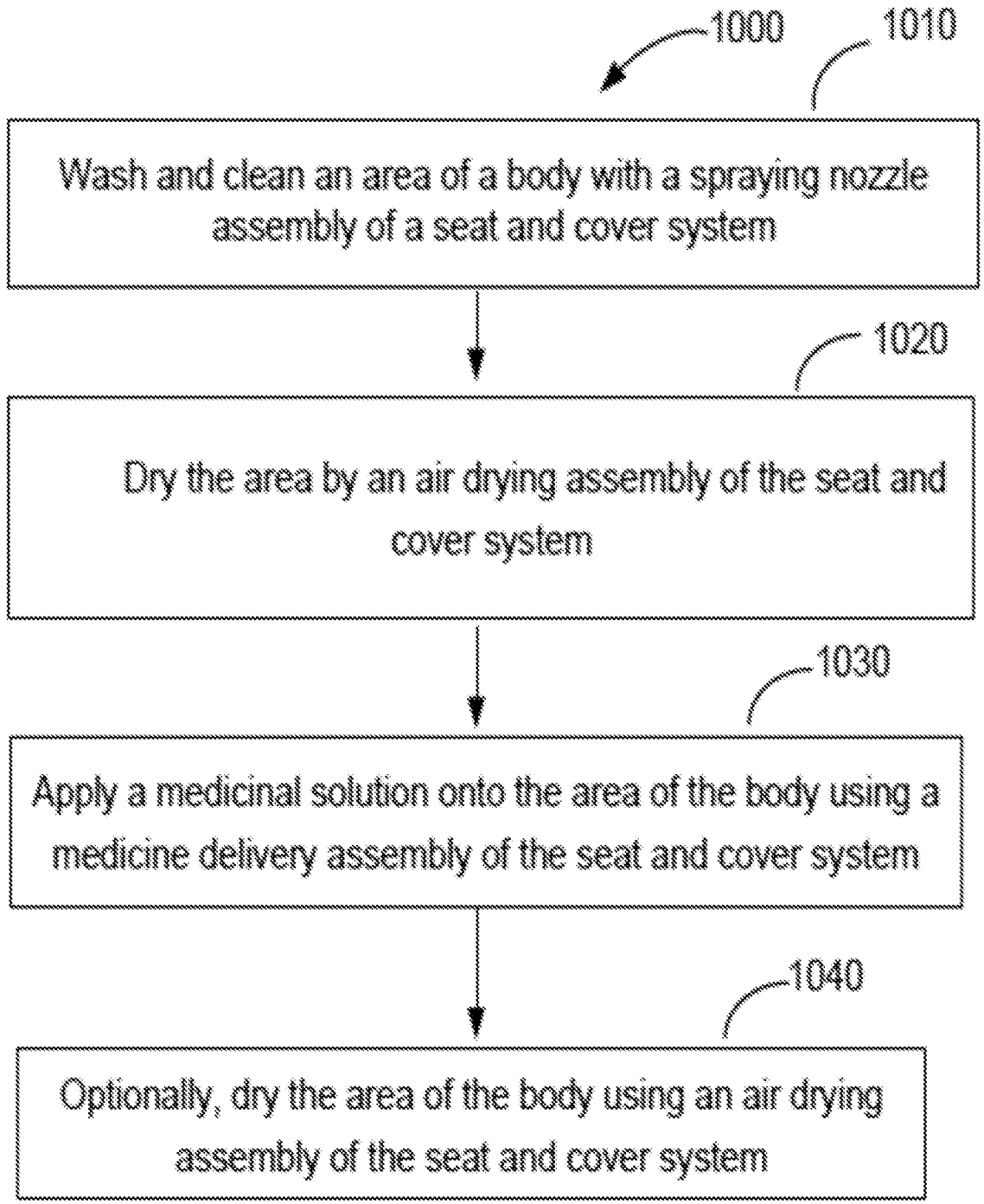
FIG. 17 is a flow chart of a method of using the system of the invention according to embodiments of the invention.

FIG. 17 is a flow chart of a method 1000 of using a seat and cover system of the invention to deliver a solution to a region of a human body. The method 1000 includes washing an area of the region with a spraying nozzle assembly of the seat and cover system at step 1010. In addition, the area of the region with the spraying nozzle assembly of the seat and cover system can be cleaned with a cleaning solution.

Step 1010 may include controlling one or more movements of a spraying nozzle assembly by one or more control units, directing one or more three-dimensional rotational movements of one or more spray nozzle units of the spraying nozzle assembly by communicating one or more control units with one or more first driving motors connected to the one or more spray nozzle units, and directing one or more extending and retracting movements of the one or more spray nozzle units of the spraying nozzle assembly by communicating the one or more control units with one or more second driving motors connected to the one or more spray nozzle units. The step 1010 may also include jetting out water from a first nozzle jet head opening of a first spray nozzle channel within the one or more spray nozzle units, and jetting out the solution from a second nozzle jet head opening of a second spray nozzle channel within the one or more spray nozzle units.

Further, during step 1010, a first spray nozzle channel is adapted to deliver water to the region of the human body for washing the region, and a second spray nozzle channel is adapted to deliver a cleaning solution to the region of the human body for cleaning the region. In another aspect, the second spray nozzle channel is adapted to deliver a medicine-containing solution to the region of the human body for treating the region. In still another aspect, a first spray nozzle channel is connected to a first liquid line to deliver a washing solution to the region of the human body for washing the region, and a second spray nozzle channel is connected to a second liquid line to deliver a cleaning solution to the region of the human body for cleaning the region. In yet another aspect, the first spray nozzle channel is connected to a first liquid line to deliver a washing solution to the region of the human body for washing the region, and the second spray nozzle channel is connected to a second liquid line to deliver a medicine-containing solution to the region of the human body for treating the region.

At step 1020, the area of the body of the user near a drying nozzle assembly of the seat and cover system is dried. The step 1020 may include controlling one or more movements of a drying nozzle assembly by one or more control units, including directing one or more three-dimensional rotational movements of one or more drying nozzle units of the drying nozzle assembly by communicating one or more control units with one or more first driving motors connected to the one or more drying nozzle units, and directing one or more extending and retracting movements of the one or more drying nozzle units of the drying nozzle assembly by communicating the one or more control units with one or more second driving motors connected to the one or more drying nozzle units.

In one embodiment, air from a drying nozzle opening is blown out at a predetermined temperature and a predetermined speed. The step 1020 may also include rotating a nozzle tip portion within the one or more spray nozzle units so that the air is adjusted to be deliver to a desired region of the human body, and adjusting one or more retractable elements within the one or more spray nozzle units by retracting and extending so that the air is adjusted to be deliver to a desired region of the human body. In addition, the step 1020 further includes receiving a user input from the drying nozzle assembly from the one or more control units, and adjusting the one or more extending and retracting movements of the one or more drying nozzle unit based on the user input. Further, the step 1020 further includes receiving a user input from the drying nozzle assembly from the one or more control units; and adjusting the one or more three-dimensional rotational movements of the one or more drying nozzle unit based on the user input.

At step 1030, a medicine-containing solution is applied onto the area using a medicine delivery assembly of the seat and cover system. The step 1030 includes providing one or more medicines to a medicine delivery assembly which is coupled to a toilet seat assembly, and controlling one or more movements of the medicine delivery assembly by one or more control units. In one aspect, controlling the movements of the medicine delivery assembly includes directing one or more extending and retracting movements of a medicine delivery nozzle of the medicine delivery assembly by communicating the one or more control units with one or more first driving motors connected to the medicine delivery nozzle, and directing one or more three-dimensional rotational movements of the medicine delivery nozzle of the medicine delivery assembly by communicating the one or more control units with one or more second motors connected to the medicine delivery nozzle.

At step 1040, optionally, the area of the body is dried again with an air drying assembly of the seat and cover system. Drying the area is performed similar to step 1020; however, the speed and temperature of the air blown to the area of the body may differ, and can be adjusted according to personal preference.

The system provided here present a safer, more hygienic, and more effective alternative method to self-administer perianal medicines than any option currently available. To this extent, the system can present a discreet, "hands-free" alternative to the current options, or couple to other system, such as a bidet toilet seat system, thereby substantially eliminating any discomfort, ineffectiveness, and/or embarrassment a user might otherwise experience.

While the foregoing is directed to embodiments of the present invention, other and further embodiments of the invention may be devised without departing from the basic scope thereof, and the scope thereof is determined by the claims that follow.

The invention claimed is:

1. An apparatus comprising:
a toilet seat assembly comprising a seat and a base;
one or more control units configured to receive a user input;
a spray nozzle assembly for cleaning at least a portion of the human body, the spray nozzle disposed at a rearward position in the toilet seat assembly;
a medicine delivery assembly adapted to deliver one or more medicine-containing solutions to the human body via the toilet seat assembly, wherein the medicine delivery assembly is housed within the base and is disposed at a forward position in the toilet seat assembly;
at least one cartridge;
a pump and a first cartridge of the at least one cartridge disposed in a side of the seat and the medicine delivery apparatus is disposed in a rear position of the seat, wherein the rear position of the seat comprises a hinged side of the seat;
wherein the pump is fluidly connected to the first cartridge, wherein the first cartridge is fluidly connected to the medicine delivery apparatus and fluidly disposed between the pump and the medicine delivery apparatus;
wherein a driving motor is operably coupled to the medicine delivery assembly, and is activated in response to a user input to thereby deliver medicine to a user.

2. The apparatus of claim 1, wherein the medicine delivery assembly further comprises one or more medicine base units, each medicine base unit comprising the at least one cartridge and at least one cartridge slot, wherein the cartridge slot is adapted to correspond with and receive the at least one cartridge.

3. The apparatus of claim 2, wherein the at least one cartridge comprises:
a cartridge cover;
a medicine inlet; and
a sensor.

4. The apparatus of claim 3, wherein the medicine delivery assembly further comprises a medicine storage assembly comprising:
a medicine storage tank adapted for storing a medicine-containing solution, the medicine storage tank having a tank cover and a tube;
wherein the tube is connected to the medicine inlet of the at least one cartridge.

5. The apparatus of claim 4, wherein the medicine storage assembly further comprises a medicine storage element adapted to store one or more medicines to be mixed with water to form the medicine-containing solution.

6. The apparatus of claim 4, wherein the medicine storage assembly further comprises a liquid solution indicator adapted to indicate the content level of the medicine-containing solution within the medicine storage tank.

7. The apparatus of claim 4, wherein the pump delivers the medicine-containing solution from the medicine storage tank into the toilet seat assembly.

8. The apparatus of claim 1, wherein the medicine delivery assembly is adapted to deliver one or more medicine-containing solutions which are stored in the at least one cartridge to the region.

9. The apparatus of claim 1, wherein the medicine delivery assembly further comprises:
one or more steering gears; and
a medicine delivery nozzle comprising a retractable nozzle body, wherein the medicine delivery nozzle is adapted to deliver one or more medicine-containing solutions to the region of the human body.

10. The apparatus of claim 9, wherein the medicine delivery nozzle further comprises an atomizer nozzle head adapted to atomize a medicine-containing solution.

11. The apparatus of claim 9, wherein the medicine delivery nozzle is adapted to deliver the medicine-containing solution across a space to a perianal region of a user.

12. The apparatus of claim 9, wherein the pump delivers the medicine-containing solution from a medicine inlet of at least one cartridge to the region.

13. The apparatus of claim 9 wherein the medicine delivery nozzle is separated from the spray nozzle assembly.

14. The apparatus of claim 1, wherein the medicine delivery assembly is coupled to a spray nozzle channel of the spray nozzle assembly.

15. The apparatus of claim 14, wherein the spray nozzle channel further comprises a nozzle jet head opening adapted to deliver the one or more solutions at high speed.

16. The apparatus of claim 15, wherein the one or more solutions are selected from the group consisting of water, a cleaning solution, a barrier spray solution, a medicine-containing solution, and combinations thereof.

17. The apparatus of claim 1, further comprising:
a drying nozzle assembly, which comprises a fan;
one or air channels connected to the fan;
one or more drying nozzle units connected to the one or more air channels; and
one or more driving motor units,
wherein the one or more driving motor units of the drying nozzle assembly further comprises:
one or more steering gears;
a first driving motor being connected to the one or more drying nozzle units and the one or more steering gears, wherein the first driving motor is adapted to move the one or more drying nozzle units in retracting-and-extending motion; and
a second driving motor being connected to the one or more drying nozzle units and the one or more steering gears, wherein the second driving motor is adapted to move the one or more drying nozzle units in three-dimensional circular rotational motion.

18. The apparatus of claim 1, wherein based on the user input, to the one or more control units, to cause movements of one or more motors and adjust the positions of one or more nozzles within the toilet seat assembly and the medicine delivery assembly.

19. An apparatus for delivering medicine to a region of a human body, comprising:
a toilet seat assembly comprising a seat and a base;
a spray nozzle assembly for cleaning at least a portion of the human body, the spray nozzle assembly disposed at a rearward position in the toilet seat assembly;
a medicine delivery assembly adapted to deliver one or more medicine-containing solutions to the toilet seat assembly, wherein the medicine delivery assembly is housed within the base, and wherein the medicine delivery assembly includes one or more nozzles and is disposed at a forward position in the toilet seat assembly;
a pump and a cartridge disposed in a side of the seat and the medicine delivery apparatus is disposed in a rear position of the seat, wherein the rear position of the seat comprises a hinged side of the seat;
wherein the pump is fluidly connected to a cartridge, wherein the cartridge is fluidly connected to the medicine delivery apparatus and fluidly disposed between the pump and the medicine delivery apparatus; and
one or more control units adapted to receive a user input and, based on the user input, to cause one or more motors to adjust the positions of the one or more nozzles.

20. A method for delivering one or more medicines to a region of a human body, comprising:
providing one or more medicines to a medicine delivery assembly which is coupled to and housed within a toilet seat assembly at a rearward position in the toilet seat assembly, wherein the toilet seat assembly comprises a seat and a base;
washing a portion of the human body via a spray nozzle assembly coupled to the toilet seat assembly, the spray nozzle disposed at a rearward position in the toilet seat assembly, separately from the medicine delivery assembly; and
disposing a pump and a cartridge in a side of the seat;
disposing the medicine delivery apparatus in a rear position of the seat, wherein the rear position of the seat comprises a hinged side of the seat;
controlling one or more movements of the medicine delivery assembly by one or more control units, wherein the controlling includes:
directing one or more extending and retracting movements of a medicine delivery nozzle of the medicine delivery assembly by communicating the one or more control units with one or more first driving motors connected to the medicine delivery nozzle.

21. An apparatus for delivering medicine to a region of a human body, comprising:
a toilet seat assembly comprising a seat and a base;
one or more control units configured to receive a user input;
a spray nozzle assembly, disposed at a rearward position in the toilet seat assembly;
a medicine delivery assembly housed within the base and is disposed at a forward position in the toilet seat assembly;
a driving motor is operably coupled to the medicine delivery assembly and is activated in response to a user input to thereby deliver medicine to a user;
a drying nozzle assembly comprises a fan, one or more air channels connected to the fan, one or more drying nozzle units connected to the one or more air channels, and
one or more driving motor units, wherein the one or more driving motor units of the drying nozzle assembly further comprises one or more steering gears;
a first driving motor being connected to the one or more drying nozzle units and the one or more steering gears, wherein the first driving motor is adapted to move the one or more drying nozzle units in retracting-and-extending motion;
a second driving motor being connected to the one or more drying nozzle units and the one or more steering gears, wherein the second driving motor is adapted to move the one or more drying nozzle units in three-dimensional circular rotational motion;
the medicine delivery assembly comprises: one or more steering gears, a medicine delivery nozzle, one or more medicine storage cartridges, a medicine storage assembly, and one or more medicine base units;
wherein each medicine base unit comprises at least a cartridge unit and at least a cartridge slot, wherein the cartridge slot is adapted to correspond with and receive a medicine storage cartridge;
wherein the medicine storage assembly comprises: a medicine storage tank adapted for storing a medicine-containing solution, the medicine storage tank having a tank cover and a tube, wherein the tube is connected to the medicine inlet of the medicine storage cartridge;
wherein the medicine storage cartridge comprises: a cartridge cover; a medicine inlet and a sensor;
wherein the medicine storage assembly comprises a medicine storage element adapted to store one or more medicines to be mixed with water to form the medicine-containing solution, a liquid solution indicator adapted to indicate the content level of the medicine-containing solution within the medicine storage tank, and a pressurized pump adapted to pump and deliver the medicine-containing solution from the medicine storage tank into the toilet seat assembly;

wherein the medicine delivery nozzle comprises a retractable nozzle body and an atomizer nozzle head adapted to atomize a medicine-containing solution, wherein the medicine delivery nozzle is: (i) adapted to deliver one or more medicine-containing solutions to the region of the human body, (ii) adapted to deliver the medicine-containing solution across a space to a perianal region of a user, (iii) separated from the spray nozzle assembly, wherein the spray nozzle comprises a nozzle jet head opening adapted to deliver the one or more solutions at high speed, wherein the one or more solutions are selected from the group consisting of water, a cleaning solution, a barrier spray solution, a medicine-containing solution, and combinations thereof; and wherein the user input to the one or more control units causes movements of one or more motors and adjusts the positions of one or more nozzles within the toilet seat assembly and the medicine delivery assembly.

22. The apparatus of claim 1, wherein a second cartridge is fluidly connected to the medicine delivery apparatus.

23. The apparatus of claim 22, wherein the second cartridge is disposed in a side of the seat different than that of the first cartridge.

24. The apparatus of claim 23, wherein the first cartridge and second cartridge are disposed along a same side as the medicine delivery apparatus.

\* \* \* \* \*